(12) United States Patent  (10) Patent No.: US 7,828,252 B2
Parsons  (45) Date of Patent: Nov. 9, 2010

(54) ADJUSTABLY POSITIONABLE DISPLAY AND LIGHTING ARRANGEMENT

(75) Inventor: Shannon G. Parsons, Waxhaw, NC (US)

(73) Assignee: TGR Intellectual Properties, LLC, Charlotte, NC (US)

( * ) Notice: Subject to any disclaimer, the term of this patent is extended or adjusted under 35 U.S.C. 154(b) by 925 days.

(21) Appl. No.: 11/275,886

(22) Filed: Feb. 1, 2006

(65) Prior Publication Data

US 2006/0104071 A1  May 18, 2006

Related U.S. Application Data

(63) Continuation of application No. 10/708,617, filed on Mar. 15, 2004, now Pat. No. 7,410,138.

(60) Provisional application No. 60/454,895, filed on Mar. 14, 2003.

(51) Int. Cl.
F16M 13/00 (2006.01)
(52) U.S. Cl. .................... 248/125.1; 248/324; 248/317; 362/11
(58) Field of Classification Search ............. 248/125.1, 248/317, 324, 343; 362/11, 251, 233, 401; 5/600
See application file for complete search history.

(56) References Cited

U.S. PATENT DOCUMENTS

| | | | |
|---|---|---|---|
| 1,070,524 A | 8/1913 | Pieper | |
| 2,215,634 A | 9/1940 | Collins et al. | |
| 2,215,635 A | 9/1940 | Collins | |
| 2,798,938 A | 7/1957 | Jewell | |
| 3,164,355 A | 1/1965 | Seitz et al. | |
| 3,240,925 A | 3/1966 | Paschke et al. | |
| 3,512,605 A | 5/1970 | McCorkle | |
| 3,547,390 A | 12/1970 | Mehr | |
| 3,950,086 A | 4/1976 | Schulman et al. | |
| 4,166,602 A | 9/1979 | Nilsen et al. | |

(Continued)

FOREIGN PATENT DOCUMENTS

EP  1544727  6/2005

OTHER PUBLICATIONS

Information Disclosure Statement (IDS) Letter Regarding Common Patent Application(s) submitted by Applicant on Aug. 30, 2010.

Primary Examiner—Anita M King
(74) Attorney, Agent, or Firm—Tillman Wright, PLLC; Chad D. Tillman; Jeremy C. Doerre

(57) ABSTRACT

An electronic display and lighting arrangement for viewing by, and illumination for, a person in a resting position includes: an electronic display assembly including a first carriage movable along a translation axis, a first pivot arm coupled to the first carriage with the first pivot arm pivotable about a first pivot axis, and an electronic display coupled to the first pivot arm; and a lighting assembly including a second carriage movable in a direction parallel to the translation axis, and a light coupled to the second carriage and adjustably positionable by movement of the second carriage. The electronic display is adjustably positionable both along the translation axis by movement of the first carriage, and about the first pivot axis by movement of the first pivot arm about the first pivot axis.

14 Claims, 14 Drawing Sheets

U.S. PATENT DOCUMENTS

| | | | |
|---|---|---|---|
| 4,503,854 A | 3/1985 | Jako | |
| 4,738,369 A | 4/1988 | Desjardins | |
| 4,812,830 A | 3/1989 | Doering | |
| 4,836,478 A | 6/1989 | Sweere | |
| 4,853,497 A | 8/1989 | Landmeier | |
| 4,881,123 A | 11/1989 | Chapple | |
| 4,931,782 A | 6/1990 | Jackson | |
| 4,934,933 A | 6/1990 | Fuchs | |
| 5,064,161 A | 11/1991 | Anderson | |
| 5,155,627 A | 10/1992 | Keehn et al. | |
| 5,201,896 A | 4/1993 | Kruszewski | |
| 5,347,431 A * | 9/1994 | Blackwell et al. | 362/11 |
| 5,405,117 A | 4/1995 | Davis | |
| 5,409,511 A | 4/1995 | Paul | |
| 5,446,339 A | 8/1995 | Kinoshita et al. | |
| 5,455,975 A * | 10/1995 | Foster | 5/600 |
| 5,471,254 A | 11/1995 | Claassen | |
| 5,515,083 A | 5/1996 | Casebolt et al. | |
| 5,519,458 A | 5/1996 | King | |
| 5,537,290 A | 7/1996 | Brown et al. | |
| 5,538,214 A | 7/1996 | Sinila | |
| 5,548,306 A | 8/1996 | Yates, IV et al. | |
| 5,579,036 A | 11/1996 | Yates, IV | |
| 5,706,290 A | 1/1998 | Shaw et al. | |
| 5,738,316 A | 4/1998 | Sweere et al. | |
| 5,754,259 A | 5/1998 | Nakamatsu et al. | |
| 5,772,174 A | 6/1998 | Hirsch | |
| 5,784,581 A | 7/1998 | Hannah | |
| 5,852,437 A | 12/1998 | Wugofski et al. | |
| 5,867,821 A | 2/1999 | Ballantyne et al. | |
| 5,923,319 A | 7/1999 | Bishop et al. | |
| 5,990,874 A | 11/1999 | Tsumura et al. | |
| 6,027,247 A | 2/2000 | Tachi et al. | |
| 6,050,833 A | 4/2000 | Danzyger et al. | |
| 6,088,069 A | 7/2000 | Farlow | |
| 6,089,518 A * | 7/2000 | Nilsson | 248/317 |
| 6,202,360 B1 * | 3/2001 | Rattner et al. | 52/36.4 |
| 6,247,768 B1 | 6/2001 | Yamaguchi | |
| 6,286,794 B1 | 9/2001 | Harbin | |
| 6,339,410 B1 | 1/2002 | Milner et al. | |
| 6,349,436 B1 * | 2/2002 | Kreuzer | 5/600 |
| 6,406,758 B1 | 6/2002 | Bottari et al. | |
| 6,431,515 B1 | 8/2002 | Gampe et al. | |
| 6,466,432 B1 | 10/2002 | Beger | |
| 6,478,274 B1 | 11/2002 | Oddsen | |
| 6,492,979 B1 | 12/2002 | Kent et al. | |
| 6,633,328 B1 * | 10/2003 | Byrd et al. | 348/143 |
| 6,639,789 B2 | 10/2003 | Beger | |
| 6,646,864 B2 | 11/2003 | Richardson | |
| 6,654,071 B2 | 11/2003 | Chen | |
| 6,659,415 B2 | 12/2003 | Kummerfeld et al. | |
| 6,677,934 B1 | 1/2004 | Blanchard | |
| 6,695,270 B1 | 2/2004 | Smed | |
| 6,712,008 B1 | 3/2004 | Habenicht et al. | |
| 6,719,253 B2 | 4/2004 | Oddsen, Jr. | |
| 6,779,767 B2 | 8/2004 | Kuhn | |
| 6,783,105 B2 | 8/2004 | Oddsen, Jr. | |
| 6,817,585 B2 | 11/2004 | Wagner et al. | |
| 6,863,252 B2 | 3/2005 | Bosson | |
| 6,899,442 B2 | 5/2005 | Howell et al. | |
| 6,900,795 B1 | 5/2005 | Knight, III et al. | |
| 6,916,065 B2 | 7/2005 | Park | |
| 6,992,659 B2 | 1/2006 | Gettemy | |
| 7,054,441 B2 | 5/2006 | Pletikosa | |
| 7,063,296 B2 | 6/2006 | Williams | |
| 7,065,811 B2 * | 6/2006 | Newkirk et al. | 5/600 |
| 7,154,397 B2 | 12/2006 | Zerhusen et al. | |
| 7,263,669 B2 | 8/2007 | Denholm | |
| 7,410,138 B2 | 8/2008 | Parsons | |
| 2001/0024685 A1 | 9/2001 | Boulton et al. | |
| 2002/0015296 A1 | 2/2002 | Howell et al. | |
| 2002/0044059 A1 | 4/2002 | Reeder et al. | |
| 2002/0074472 A1 | 6/2002 | Gaida et al. | |
| 2003/0052787 A1 | 3/2003 | Zerhusen et al. | |
| 2003/0197688 A1 | 10/2003 | Aufderheide et al. | |
| 2004/0007907 A1 | 1/2004 | Dire | |
| 2006/0001740 A1 | 1/2006 | Fujie et al. | |
| 2006/0103636 A1 | 5/2006 | Parsons | |
| 2006/0108484 A1 | 5/2006 | Parsons | |
| 2006/0113436 A1 | 6/2006 | Parsons | |
| 2006/0113437 A1 | 6/2006 | Parsons | |
| 2006/0113438 A1 | 6/2006 | Parsons | |
| 2006/0113439 A1 | 6/2006 | Parsons | |
| 2006/0113445 A1 | 6/2006 | Parsons | |
| 2006/0113446 A1 | 6/2006 | Parsons | |
| 2006/0113447 A1 | 6/2006 | Parsons | |
| 2006/0113448 A1 | 6/2006 | Parsons | |
| 2006/0132594 A1 | 6/2006 | Parsons | |
| 2006/0138288 A1 | 6/2006 | Parsons | |
| 2006/0175477 A1 | 8/2006 | Parsons | |
| 2007/0199023 A1 | 8/2007 | Small et al. | |

* cited by examiner

ADJUSTABLY POSITIONABLE DISPLAY AND LIGHTING ARRANGEMENT

CROSS REFERENCE TO RELATED APPLICATIONS

The present application is a continuation of, and claims priority under 35 U.S.C. section 120 to, U.S. nonprovisional patent application Ser. No. 10/708,617, filed Mar. 15, 2004, which application is hereby incorporated by reference herein, and which application is a nonprovisional patent application of, and claims priority under 35 U.S.C. section 119(e) to, U.S. provisional patent application Ser. No. 60/454,895, filed Mar. 14, 2003, which provisional patent application is incorporated by reference herein.

BACKGROUND OF INVENTION

Modern healthcare providers are learning that true healthcare involves much more than perfunctory attention to physical ailments. The best care embraces the full spectrum of needs of a patient. A patient that is comfortable with attention and treatment is indeed likely to benefit from participation in preventive practices and regularly scheduled appointments for care. Indeed, preventive medicine is thought to be a key to the future in lowering healthcare costs and in improving quality of life.

A distraction from what may otherwise be an uncomfortable or awkward procedure can help a patient relax and can thereby reduce both physical and mental stress and increase the tolerance of the patient during a lengthy procedure. If improvements to the full experience of the patient can be achieved, then the patient is more likely to pursue elective care services. This may be of particular importance in, for example, the oral care industry where dentists have suffered since the conception of their craft against a reputation for providing needed but often uncomfortable services to patients.

Even routine healthcare services such as oral hygiene procedures can provide a less than optimal patient experience. Patients are typically at least bored while receiving such care. The overall experience of the patient could be substantially improved by some convenient arrangement for entertainment.

In addressing the need for patient distractions, many dentists now incorporate into the provision of healthcare the presentation of audio and/or video content to patients while the patients are receiving healthcare services. In this regard, computer monitors and televisions, headphones, and even virtual reality goggles are provided in order to provide patient distraction from dental procedures. The monitors and televisions are incorporated into the dental treatment rooms by positioning them into or on top of cabinets in the treatment rooms, or mounting them on arms attached to dental chairs. The view of these monitors and televisions provided to the patient, however, is less than optimal, as many dental procedures require the patient to be fully reclined in the dental chair. Headphones also inhibit effective communication between the patient and provider of the healthcare service during the procedure. Virtual reality goggles may be similarly obstructive and are not comfortable to some patients who experience claustrophobia.

Accordingly, a need continues to exist for improvements in the provision of healthcare and, especially, dental healthcare. This, and other needs, are addressed by one or more aspects of the present invention.

SUMMARY OF INVENTION

The present invention includes many aspects and features. Moreover, while many aspects and features relate to, and are described in, the context of the provision of healthcare, and especially dental healthcare, the present invention is not limited to use only in the provision of healthcare, as will become apparent from the following summaries and detailed descriptions of aspects, features, and preferred embodiments of the present invention.

Accordingly, one aspect of the present invention relates to an electronic display assembly for viewing by a person in a "resting position." An exemplary such assembly includes an arm that is rotatable about a swivel axis, an arm that is pivotable about a pivot axis and is coupled to the rotatable arm, and an electronic display that is coupled to the pivotable arm and that is "adjustably positionable" about the swivel axis and about the pivot axis. As used herein, the phrase "resting position" pertains to a seated, reclined, lying, or in some way supported physical situation of a person. Similarly, the phrase "adjustably positionable" pertains to the ability to be positioned in various places through translational movement, through rotational movement, or a combination of both.

Another aspect of the invention relating to an electronic display assembly for viewing by a person in a resting position includes a carriage movable along a translation axis, a swivel arm coupled to the carriage and rotatable about a swivel axis, a pivot arm coupled to the swivel arm and pivotable about a pivot axis, and an electronic display coupled to the pivot arm. The display of this aspect is adjustably positionable along the translation axis, about the swivel axis, and about the pivot axis. Furthermore, through a range of adjustable positioning of the display, the swivel axis remains orthogonal to the translation axis, and the pivot axis remains non-orthogonal to the translation axis.

An aspect of the present invention relating to a variably adjustable electronic display assembly for viewing by a person in a resting position includes a carriage movable along a translation axis, a swivel arm coupled to the carriage, a pivot arm coupled to the swivel arm, and an electronic display coupled to the pivot arm. In this aspect, the swivel arm is rotatable about a first swivel axis so that the swivel arm, the pivot arm, and the electronic display, together, are adjustably positionable about the first swivel axis. Furthermore, in this aspect of the invention, the swivel arm is rotatable about a second swivel axis, so that the pivot arm and the electronic display, together, are adjustably positionable about the second swivel axis independent of the adjustable positioning of the swivel arm. Also in this aspect, the pivot arm is pivotable about a first pivot axis and a second pivot axis so that the pivot arm and the electronic display, together, are adjustably positionable about the first pivot axis and second pivot axis independent of the adjustable positioning of the swivel arm. Still yet in this aspect, the electronic display is pivotable about a third pivot axis so that the display is adjustably positionable about the third pivot axis independent of the adjustable positionings of the pivot arm. The display is also rotatable about a third swivel axis to be adjustably positionable about the third swivel axis independent of the adjustable positionings of the pivot arm.

Another aspect of the present invention relating to an electronic display assembly for viewing by a person in a resting position includes an electronic display supported by a pivot arm that is coupled to a carriage. The carriage is movable along a translation axis and the arm is pivotable about a pivot axis. The display is adjustably positionable along the translation axis and about the pivot axis through a range of positioning wherein the pivot axis remains non-orthogonal to the translation axis. In a feature of this aspect of the invention, the electronic display is suspended below the carriage and the carriage is coupled to a track for movement along the translation axis. Optionally, the track is mounted to a ceiling or wall. In other features of this aspect, a subassembly couples the electronic display to the pivot arm. In one embodiment the subassembly is a display bracket, and in the same or another embodiment the subassembly includes a swivel member through which a swivel axis passes, a display mounting member, and an elongate member that extends between the swivel member and the mounting member and that is rotatable about the swivel axis. Furthermore, the elongate member is pivotably mounted to the swivel member for pivoting movement about a second pivot axis, and is pivotably mounted to the mounting member for pivoting movement about a third pivot axis. In additional features, the pivot arm is pivotable about another pivot axis that passes through an end of the pivot arm that is disposed adjacent to the electronic display, and the pivot arm is constructed as a four-bar-linkage parallelogram.

Yet another aspect of the present invention relates to an electronic display assembly for viewing by a person in a resting position and includes a carriage movable along a translation axis, a swivel arm coupled to the carriage, a swivel arm rotatable about a swivel axis, and an electronic display that is coupled to the swivel arm and that is adjustably positionable both along the translation axis and about the swivel axis. In this aspect the swivel axis remains orthogonal to the translation axis throughout adjustable positioning of the electronic display. In a feature of this aspect, the electronic display is suspended below the carriage.

Another aspect of the present invention relates to an electronic display and lighting arrangement for viewing by, and illumination for, a person in a resting position. In this arrangement an electronic display may be adjustably positioned so that viewing is unobstructed by a light providing illumination. The electronic display assembly of this aspect includes a first carriage movable along a translation axis, a first pivot arm that is coupled to the first carriage and that is pivotable about a first pivot axis, and an electronic display coupled to the first pivot arm. The electronic display is adjustably positionable along the translation axis by movement of the first carriage, and about the first pivot axis by movement of the first pivot arm about the first pivot axis. The lighting assembly of this aspect includes a second carriage movable in a direction parallel to the translation axis, and a light coupled to the second carriage and adjustably positionable by movement of the second carriage. In one embodiment of this aspect, the first carriage and second carriage are coupled to the same track and are both movable along the translation axis. In this aspect, the track is mounted to a ceiling and the electronic display and light are suspended, respectively, from their own separate carriages.

Another aspect of the present invention that relates to an electronic display and lighting arrangement for viewing by, and illumination for, a person in a resting position includes a carriage movable along a translation axis, a pivot arm coupled to the carriage and pivotable about a pivot axis, an electronic display coupled to the pivot arm, and a light mounted to the electronic display. The electronic display is adjustably positionable both along the translation axis by movement of the carriage, and about the pivot axis by movement of the pivot arm. Illumination by the light may be provided for the person in the resting position and the electronic display may be adjustably positioned for viewing by the person unobstructed by the light.

Yet another aspect of the invention relating to an electronic display and lighting assembly for viewing by, and illumination for a person in a resting position, includes a carriage movable along a translation axis, a vertical support member coupled to the carriage, an electronic display, and a light. The electronic display is coupled to the vertical support member by a first swivel arm and is adjustably positionable both along the translation axis by movement of the carriage, and about a vertical axis of the support member by rotational movement of the swivel arm about the vertical axis. The light is coupled to the vertical support member by a second swivel arm and is adjustably positionable both along the translation axis by movement of the carriage, and about the vertical axis by rotational movement of the second swivel arm about the vertical axis. Illumination by the light may be provided for the person in the resting position and the electronic display may be adjustably positioned for viewing by the person unobstructed by the light.

Another aspect of the present invention relates to an electronic display assembly for viewing by a person in a resting position. The assembly includes a pivot arm pivotable about a pivot axis, an electronic display coupled to the pivot arm to be adjustably positionable about the pivot axis, and a counterweight coupled to the pivot arm opposing the display about the pivot point. In features of this aspect, the counterweight has a greater mass than that of the electronic display, the counterweight is located closer to the pivot point than the electronic display, and the counterweight has a moment about the pivot point that is within an order of magnitude of a moment of the display about the pivot point.

Another aspect of the invention, relating to an electronic display assembly for viewing by a person in a resting position, includes an apparatus for receiving a person in a resting position, a support, and an electronic display coupled to the support such that the display is adjustably positionable above the apparatus along each of three orthogonal axes for convenient viewing by a person in a resting position received in the apparatus. In a feature of this aspect, the electronic display assembly is adjustably positionable along a first of the three orthogonal axes independent of adjustable positioning along the other two. In another feature, the electronic display is adjustably positionable along each of the three orthogonal axes independently. In other words, the display is adjustably positionable along any particular one of the axes independently of its positioning along the other two.

Yet another aspect of the invention relating to an electronic display assembly for viewing by a person in a resting position includes an apparatus for receiving a person in a resting position, a support including a carriage suspended above and movable over the apparatus along a translation axis, and an electronic display coupled to the support. The display is adjustably positionable both in a first direction parallel to the translation axis, and in a second direction orthogonal to the first direction. In a feature of this aspect, the electronic display is adjustably positionable in the first direction independent of its adjustable positioning along the second direction.

Another aspect of the invention relates to an electronic display assembly for viewing by a person in a resting position and includes a carriage movable along a translation axis, a pivot arm coupled to the carriage, a pivot arm pivotable about a pivot axis, and a subassembly coupled to the pivot arm. The subassembly includes an electronic display, for presenting video, and an electronic input member. The display is adjustably positionable along the translation axis by movement of the carriage, and about the pivot axis by movement of the pivot arm about the pivot axis. In a feature of this aspect, the input member may be, for example, a touchscreen or an antenna for receiving wireless transmissions. The input member also may be, for example, an electronic communications port. In this regard, exemplary ports include, but are not limited to, a USB port, a firewire port, a serial port, a parallel port, and a PS/2 port. Alternatively, the input member may be, for example, a data acquisition device that, preferably, is mounted to the subassembly. Exemplary devices include, but are not limited to, a sensor, a camera, and a microphone. In another feature of this aspect, a computer is disposed in electronic communication with the electronic input member for receiving data from the electronic input member. In one such embodiment, the computer manages presentation of video on the electronic display, and data received from the electronic input member represents instructions to the computer for managing the presentation of the video on the electronic display. Additionally, in features of this aspect, the subassembly includes the computer and the computer is coupled to the pivot arm. In other features, the computer is stationary and does not move with movement of the carriage, the pivot arm, or the subassembly. In additional features of this aspect, the electronic input member comprises, for example, a conducting contact, an electromechanical switch, a mouse, a handheld device, a joystick, a keyboard, a keypad, a touchscreen, and/or a wireless communications device. The control by the patient includes, for example, the selecting, by the patient, for presentation on the electronic display, of a movie, a television station, a cable station, a satellite station, a music video, an educational video, and/or a cartoon. In other features, the content presented by the electronic display comprises video output from a computer. In such cases, the control by the patient includes, for example, navigating the Internet, reading email, and/or composing email.

Another aspect of the present invention also relates to an electronic display assembly for viewing by a person in a resting position. In accordance with this aspect, the assembly includes an apparatus for receiving a person in a resting position, an overhead support, an electronic display coupled to the support such that the electronic display is adjustably positionable above the apparatus whereby the electronic display may be conveniently viewed by a person in a resting position received in the apparatus, a send unit operative for sending signals conveying visual content for presentation by the electronic display, and a receive unit operative for receiving the signals sent by the send unit and disposed in electronic communication with the electronic display for presenting the visual content of the signals received by the receive unit. In features of this aspect, the receive unit is coupled to the overhead support and the send unit is not coupled to the overhead support. In other features, the receive unit is coupled to the electronic display for concurrent movement therewith and the receive unit is coupled to the overhead support in fixed location. In additional features, the send unit may be disposed in electronic communication with the receive unit by a cable for carrying signals from the send unit to the receive unit, or the send unit may include a transmitter for broadcasting a wireless signal to the receive unit. For example, the send unit may comprise a radio frequency (RF) transmitter for sending a wireless signal to the receive unit. In other features, the send unit is further operative for sending additional signals conveying auditory content, and the assembly further includes an audio unit for receiving the additional signals and for producing sound to convey the auditory content. In still other features, the assembly further includes a speaker system for receiving additional signals from the send unit and producing sound represented by the additional signals. The assembly also further may include a headphone set for receiving additional signals from the send unit and producing sound represented by the additional signals to convey auditory content in conjunction with presented visual content. The send unit also may include a plurality of inputs for receiving signals conveying visual content, such inputs including, for instance, an S video input, a cable input, a USB input, and/or an RCA input. In other features of this aspect, the assembly further includes an electronic input member for receiving input from a person regarding controlling presentation of visual content by the electronic display, with the electronic input member being disposed in electronic communication with the receive unit. In this case, the receive unit may be operative, in response to input received by the electronic input member, for sending signals to the send unit for controlling presentation of visual content by the electronic display, whereby the send unit is operative for receiving the signals controlling presentation of visual content from the receive unit.

In an aspect of the present invention that does relate specifically to providing healthcare service to a patient, a method includes the steps of providing an apparatus for receiving a patient in a resting position, suspending an electronic display above the provided apparatus with the patient received therein in a resting position, and adjustably positioning the display to be conveniently viewed by the patient while receiving healthcare service. The step of adjustably positioning the display includes independently moving the display along three axes that are mutually orthogonal.

In another such aspect of the present invention, a method for providing healthcare service to a patient includes the steps of providing an apparatus for receiving a patient in a resting position, suspending an electronic display above the provided apparatus with the patient received therein in a resting position, adjustably positioning the suspended electronic display whereby the electronic display may be conveniently viewed by the patient in the resting position in the apparatus while receiving healthcare service, and providing an electronic input member for use by the patient in controlling video presented by the electronic display. Furthermore, the step of adjustably positioning the display includes moving, in combination, the display in a first direction parallel to the translation axis, and in a second direction orthogonal to the first direction.

In yet another such aspect, a method for providing healthcare service to each of a plurality of patients includes the steps of, for each patient, providing an apparatus for receiving the patient in a resting position, suspending an electronic display above the provided apparatus with the patient received therein in a resting position, adjustably positioning the suspended electronic display whereby the electronic display may be conveniently viewed by the patient in the resting position in the apparatus while receiving healthcare service, providing an electronic input member for use by the patient or a healthcare provider in controlling video presented by the electronic display, receiving electronic input regarding video presented by the electronic display, and delivering video in accordance with the received electronic input for presenting by the electronic display. The step of delivering video may be performed contemporaneously for each of the plurality of patients. Furthermore, in a feature of this aspect, the delivered video for each patient preferably includes media content that is selected by the patient from a plurality of available video content selections. The available video content selections may be stored at a central distribution system. In features of this aspect, the healthcare care service is provided to each of the plurality of patients at the same healthcare facility, and the central distribution system is located on premises at the healthcare facility. Alternatively, the healthcare service is provided to each of the plurality of patients at a different healthcare facility, and the central distribution system is located either on premises at one of the healthcare facilities or remote to each of the different healthcare facilities. In either of these two cases, the step of delivering video may include, for one or more patients, communicating over the Internet. Moreover, the central distribution system itself preferably includes at least one data storage device for digitally storing the available video content selections, which device may include, for example, a computer readable medium containing the video content selections, computer memory, and/or one or more optical discs. In other various features of this aspect, the delivered video comprises a movie, television programming, cable programming, satellite programming, a music video, an educational video, a cartoon, and/or even a live video feed from a camera such as, for example, a camera coupled to the suspended electronic display for recording of the provision of healthcare service. In still other features, the delivered video also may comprise, for instance, output from a computer, wherein the output may comprises video representing an Internet webpage, video displaying an Internet webpage, and/or video displaying email. The delivered video also may include audio.

In yet other variations of this aspect of the present invention, simply audio content rather than video content may likewise be stored and delivered. Of course, in these variations, an electronic display may or may not be provided so long as a speaker component is provided for presenting the audio content.

Another such aspect of the present invention relating specifically to providing healthcare service to each of a plurality of patients includes a system having, for each patient, an apparatus for receiving the patient in a resting position, an electronic display suspended above the apparatus and adjustably positionable for convenient viewing by the patient in the resting position in the apparatus while receiving healthcare service, and an electronic input member for use by the patient or a healthcare provider in controlling video presented by the electronic display. The system further includes, for all patients, a central distribution system for receiving for each patient electronic input regarding video presented by the respective electronic display viewed by each patient, and for delivering video in accordance with the received electronic input for presenting by the respective electronic display viewed by each patient. In features of this aspect of the present invention, the central distribution system includes a plurality of available video content selections from which each patient may choose for presenting by the respective electronic display viewed by the patient. Furthermore, the healthcare service is provided to each of the plurality of patients at the same healthcare facility, and the central distribution system is located on premises at the healthcare facility. Alternatively, the healthcare service is provided to each of the plurality of patients at a different healthcare facility, and the central distribution system is located on premises at one of the healthcare facilities or remote to each of the different healthcare facilities. In these cases, the central distribution system preferably communicates over the Internet with at least one of the healthcare facilities. In additional features of this aspect, the central distribution system is maintained by the entity responsible for providing the healthcare service or, alternatively, by a third-party responsible for delivering the video in accordance with the present invention. If provided by a third-party, then the delivery of the video may be provided for a fee under a subscription contract or on demand on a pay-per-view basis. In still other features, the central distribution system includes at least one data storage device for digitally storing available video content selections, such device including, for example, a computer readable medium containing the video content selections, computer memory, and/or one or more optical discs. The delivered video may include, for example, a movie, television programming, cable programming, satellite programming, advertisements, a music video, an educational video, a cartoon, and/or audio. If advertisements are presented, then the advertisements may pertain to the healthcare service provided.

In yet other variations of this aspect of the present invention, simply audio content rather than video content may likewise be stored and delivered. Of course, in these variations, an electronic display may or may not be provided so long as a speaker component is provided for presenting the audio content.

Another such aspect of the present invention relates to an electronic display arrangement for viewing of video by a person receiving a healthcare service in a resting position. The arrangement of this aspect includes an apparatus for receiving a patient in a resting position, an electronic display suspended above the apparatus and adjustably positionable for unobstructed viewing by the patient receiving a healthcare service from a healthcare service provider, a computer system including healthcare software having data pertaining to the healthcare service received by the patient, with the computer system being disposed in electronic communication with the electronic display for presenting, by the electronic display in accordance with instructions of the healthcare software, video output from the computer system, and a computer input member for use by the healthcare service provider for interfacing with the healthcare software of the computer system while the patient is receiving the healthcare service. In features of this aspect, the computer input member communicates with the computer system through the electronic display suspended above the apparatus, and the computer input member comprises, for instance, a touchscreen of the electronic display. Alternatively, the computer input member comprises, for example, a keypad, a keyboard, a mouse, or an electromechanical switch. In other features of this aspect, the healthcare service received by the patient comprises dental care, the video output represents a healthcare record of the patient, and/or the video output represents information regarding the healthcare service being received by the patient such as, for example, a procedure to be performed upon the patient.

Another method of providing a healthcare service to a patient in a resting position, in accordance with another aspect of the present invention, includes the steps of providing an apparatus for receiving a patient in a resting position, suspending an electronic display above the apparatus and adjustably positioning the electronic display for unobstructed viewing by the patient receiving a healthcare service, and using a computer input member to interface with a computer system including healthcare software having data pertaining to the healthcare service received by the patient, with the computer system being disposed in electronic communication with the suspended electronic display. Furthermore, the step of using the computer interface includes controlling the presentation, by the electronic display in accordance with instructions of the healthcare software, of video output from the computer system while the patient is receiving the healthcare service.

In yet another aspect of the present invention pertaining to providing healthcare, a method of interfacing with a computer system having healthcare software having data pertaining to a healthcare service received by a patient includes the steps of suspending an electronic display above an apparatus for receiving the patient in a resting position, adjustably positioning the electronic display for unobstructed viewing by the patient receiving therein the healthcare service, and communicating with the computer system through a computer input member that communicates with the computer system through the electronic display suspended above the apparatus. In features of this aspect, the step of communicating with the computer system includes controlling presentation by the suspended electronic display of video output from the computer system while the patient is receiving the healthcare service, with the computer system being disposed in electronic communication with the suspended electronic display for presenting video. In this regard, the video output preferably is generated by the computer system in accordance with instructions of the healthcare software.

An aspect of the present invention pertaining to providing healthcare includes an electronic display arrangement for viewing of video, wherein the person viewing the video is a patient receiving a healthcare service in a resting position or is a healthcare provider providing such healthcare service. The arrangement of this aspect of the present invention includes an apparatus for receiving a patient in a resting position, and an electronic display suspended above the apparatus and adjustably positionable for unobstructed viewing by the person. Furthermore, the electronic display includes a display screen and a protective member covering the display screen. In the feature of this aspect, the display screen comprises a touchscreen that, for example, is an infrared touchscreen or that utilizes projected capacitive technology. The protective member preferably is transparent and is removably attached to the electronic display, whereby the protective member may be replaced from time-to-time, as needed. For example, the protective member may be removably attached to the electronic display by a plurality of screws. In still other features, the protective member itself preferably comprises a polycarbonate material sold by General Electric under the trademark "LEXAN"; however, the protective member generally may comprise, for instance, a plastic material, a thermoplastic material, and/or a chemical-resistant material, and the protective member may include, for instance, scratch resistant characteristics, antistatic characteristics, antiglare characteristics, and impact resistant characteristics. The protective member also preferably is waterproof and impenetrable to pathogens. Moreover, the protective member preferably is screen printed with a black color on an inside surface thereof to present a solid black appearance to a viewer when the underlying display screen is not illuminated. In still other features of this aspect, a polarizing filter and/or a Bernoulli lens is disposed between the display screen and the protective member to improve visibility of the image presented to the patient.

In yet another aspect of the present invention, an electronic display arrangement for viewing of video by a person, who is a patient receiving a healthcare service in a resting position or who is a healthcare provider providing such healthcare service, includes an apparatus for receiving a patient in a resting position, and an electronic display suspended above the apparatus and adjustably positionable for unobstructed viewing by the person, wherein the electronic display includes a touchscreen and a protective shield overlying the touchscreen.

A method, in accordance with an aspect of the present invention relating to providing a healthcare service to a patient in a resting position, includes the steps of providing an apparatus for receiving a patient in a resting position, suspending an electronic display above the apparatus and adjustably positioning the electronic display for unobstructed viewing by a person who is a patient receiving a healthcare service in a resting position or who is a healthcare provider providing such healthcare service, and protecting the electronic display suspended above the provided apparatus by securing a protective shield over the electronic display. In features of this aspect, the method further includes such steps as interfacing with a computer system in communication with the electronic display by utilizing a touchscreen of the electronic display disposed beneath the protective shield, sterilizing the protective shield with a disinfectant, and detaching the protective shield from the electronic display and attaching a new protective shield to the electronic display The protective shield itself preferably is transparent and is made, for example, from a polycarbonate material.

In accordance with yet another aspect of the present invention, an audio communication system for use between a patient receiving a healthcare service and a healthcare provider includes a speaker component for providing auditory content to the patient while receiving the healthcare service, an audio component in communication with the speaker component for providing the auditory content to the speaker component, and an input controller accessible to the healthcare provider for controlling the provision of the auditory content to the patient. In a feature of this aspect, the audio communication system includes a microphone component by which the healthcare provider speaks to the patient through the speaker component. The microphone component may communicate directly with the audio component for conveying the voice of the healthcare provider to the patient or directly with the speaker component for conveying the voice of the healthcare provider to the patient. In other features, the input controller comprises a foot actuated switch or pedal, and the input controller is disposed in communication with either the speaker component or the audio component for varying the volume of, or muting, the auditory content provided to the patient while receiving the healthcare service. In still other features, the input controller is disposed in communication with the audio component for selecting auditory content to be provided to the patient. The audio communication system also preferably includes a second input controller disposed in communication with the audio component for controlling, by the patient, the provision of the auditory content. The speaker component may comprises, for example, headphones or earphones for wearing by the patient. The speaker component alternatively may comprise, for example, a speaker coupled to, or embedded in, the apparatus. If embedded in the apparatus, the speaker preferably is embedded in a headrest of the apparatus in order to be in close proximity to a patient's head. In still other features, the audio component communicates wirelessly with the speaker component, in which case the speaker component preferably includes a wireless signal receiver for receiving signals conveying the auditory content. In this regard, the wireless signal receiver may include a radio-frequency (RF) or infrared (IR) signal receiver. Additionally, the audio communications system preferably further includes a storage component wherein a plurality of auditory content selections are stored, with the storage component being disposed in communication with the audio component for providing, by the audio component, any one of the auditory content selections to the speaker component. The storage component may include, for example, a digital jukebox and/or a DVD jukebox. The storage component also may be a computer readable medium and the audio component may be a computer.

An audiovisual system for use in providing a healthcare service to a patient by a healthcare provider includes, in accordance with another aspect of the present invention, a speaker component for providing auditory content to the patient while receiving the healthcare service, an electronic display for providing visual content to the patient while receiving the healthcare service, an audiovisual component in communication with the electronic display for providing the visual content to the electronic display and in communication with the speaker component for providing the auditory content to the speaker component in conjunction with the visual content, and an input controller accessible to the healthcare provider for the controlling of the provision of the auditory content to the patient. In features of this aspect, the audiovisual system further includes a microphone component by which the healthcare provider speaks to the patient through the speaker component, and the speaker component is coupled to the electronic display.

In certain features of embodiments of these aspects, the electronic display is suspended above an apparatus for receiving a person. In this regard, the apparatus may be a medical support apparatus, such as a dental chair or an operating table, or the apparatus may be a bed, chair, or recliner such as is found in a home.

In addition to the aforementioned aspects and features of the present invention, it will be noted that the present invention further includes all combinations of such aspects and features. Thus, for example, any of the broad aspects of the present invention may be utilized in providing healthcare service to one or more patients, including dental healthcare. Similarly, any of the assemblies and arrangements of the aspects of the present invention may be utilized in presenting video to one or more patients. Such additional aspects and features will be apparent from detailed description of preferred embodiments of the present invention, as now described below.

BRIEF DESCRIPTION OF DRAWINGS

Aspects of the present invention, in conjunction with preferred embodiments and a commercial product, will now be described in detail with reference to the accompanying drawings, wherein the same elements are referred to with the same reference numerals, and wherein.

DETAILED DESCRIPTION

As a preliminary matter, it will readily be understood by those persons skilled in the art that the present invention is susceptible of broad utility and application in view of the following detailed description of preferred embodiments. Furthermore, many embodiments as well as adaptations, variations, modifications, and equivalent arrangements, will be apparent from or reasonably suggested by the preferred embodiments described herein without departing from the scope of the present invention. Accordingly, while the present invention is described herein in detail in relation to preferred embodiments, it is to be understood that this disclosure is illustrative and exemplary and is made merely for purposes of providing a full and enabling disclosure of the present invention. The disclosure herein is not intended, nor is to be construed, to limit the scope of the present invention, which is defined by the claims and the equivalents thereof.

Figure 1:
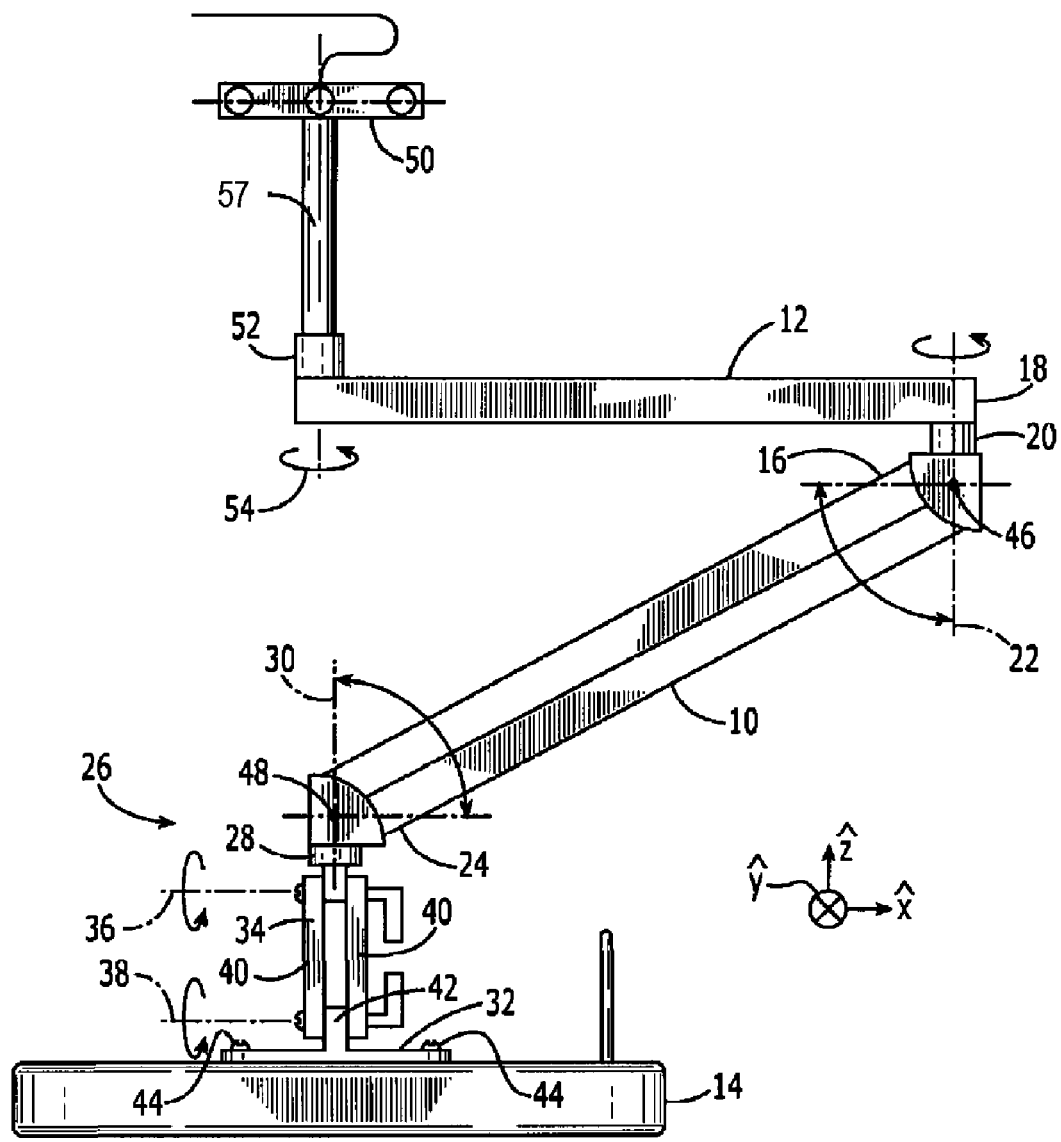
FIG. 1 is an elevational plan view of a preferred embodiment of an electronic display assembly in accordance with one or more aspects of the present invention.
Figure 2:
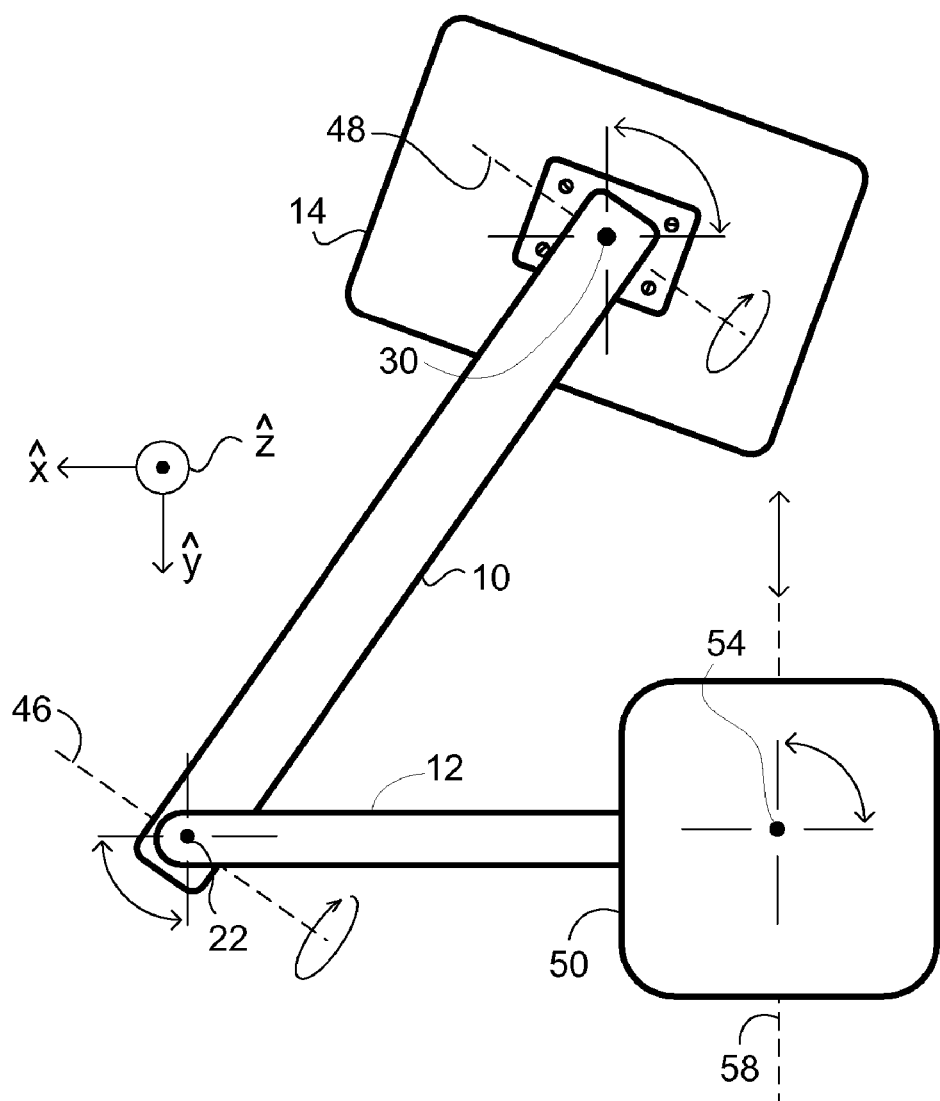
FIG. 2 is a plan schematic view of the electronic display assembly of FIG. 1.

Turning now to FIG. 1, a preferred embodiment of an electronic display assembly of the present invention is illustrated from a elevational side view, and further is illustrated from a plan view in FIG. 2. This preferred embodiment includes a pivot arm 10, a swivel arm 12, and an electronic display 14. The pivot arm 10 is coupled at a distal end 16 thereof to a distal end 18 of the swivel arm 12. The coupling is accomplished by a swivel 20 such that the pivot arm 10 can be variably swiveled about a swivel axis 22 passing through the swivel 20. Similarly, the other distal end 24 of the pivot arm 10 is coupled to the electronic display 14.

In this regard, a subassembly 26 couples the pivot arm 10 to the electronic display 14, and includes a swivel 28 through which a swivel axis 30 passes, a mounting member 32, and an elongate member 34 extending between and connecting together the swivel 28 and the mounting member 32. The elongate member 34 is pivotably mounted to the swivel member 28 for pivoting movement about pivot axis 36. The elongate member 34 also is pivotably mounted to the mounting member 32 for pivoting movement about pivot axis 38. The elongate member 34 is rotatable about the swivel axis 30 and includes two elongate side bars 40. The coupling of the elongate member 34 to the swivel 28 includes a post that extends downwardly from the swivel 28, to which both elongate bars 40 are directly secured by a first clamp bolt assembly and nut. Similarly, both elongate bars 40 are directly secured to a post portion 42 of the of the mounting member 32 by a second clamp bolt assembly and nut. The mounting member 32 is removably attached via screws 44 directly to the electronic display 14 in fixed relation thereto.

The pivot arm comprises a pair of parallel elongate members joined to form a four-bar-linkage parallelogram, and the pivot arm 10 is pivotable about a pivot axis 46 and another pivot axis 48. The pivot axis 46 passes through the distal end 16 of the pivot arm 10, and the pivot axis 48 passes through the distal end 24 of the pivot arm 10. As will be appreciated by one having ordinary skill in the art, the design of the pivot arm 10 is such that raising or lowering of the electronic display 14 by pivoting movement of the pivot arm 10 about both pivot axes 46,48 permits the swivel axes 22,30 to remain in parallel relation.

The swivel arm 12 preferably is mounted to a ceiling of a room but, alternatively, may be mounted to a wall or other support. This mounting may be accomplished by coupling the distal end 18 of the swivel arm 12 to a carriage 50. This coupling is accomplished by a swivel 52 such that the swivel arm 12 can be variably swiveled about a swivel axis 54 passing through the swivel 52, and a vertical member 57 that extends between and connects this swivel 52 to the carriage 50. The vertical member 57 is of sufficient mechanical strength to physically withstand the tensile, shear, and torsional forces of supporting the electronic display 14 and its coupling to the vertical member 57 in their suspension below the carriage 50. The swivel arm 12, in turn, includes sufficient mechanical strength to physically withstand the tensile, shear, and torsional forces of supporting the electronic display 14 and its coupling to the swivel arm 12 in their suspension below the carriage 50.

Each of the aforementioned swivels may include any suitable construction and arrangement of bearings, races, cones, axles, or bushings to allow rotation.

Figure 3:
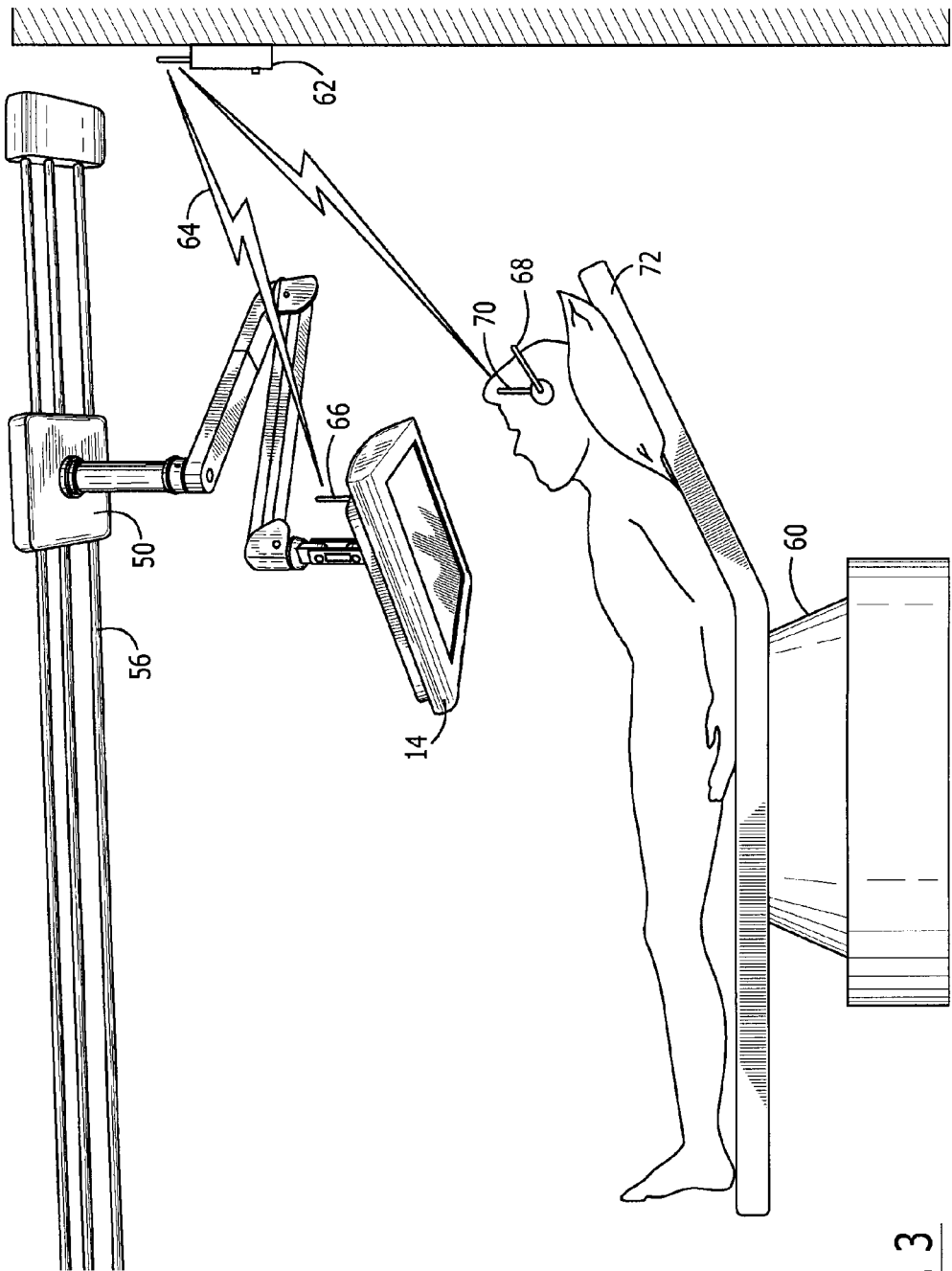
FIG. 3 is a perspective elevational view of a preferred embodiment of an electronic display assembly in accordance with one or more aspects of the present invention.

As best shown in FIG. 3, the carriage 50 itself is secured to a ceiling-mounted track 56 such that the carriage 50 can be variably positioned along the overhead track 56 that extends generally parallel to the ceiling and that defines a translational axis. Translational movement of the carriage 50 along the overhead track 56 results in simple translational movement of, inter alia, the electronic display 14. The carriage 50 may be movably mounted to the track 56 by way of bearings, rollers, glide bushings, collars and shafts, or any suitable mechanical coupling allowing the carriage 50 to be variably positioned along the track 56.

As will be appreciated from the foregoing description, and as shown in FIG. 2, the swivel arm 12 is rotatable about the swivel axis 54, whereby the swivel arm 12, the pivot arm 10, and the electronic display 14, together, are adjustably positionable about the swivel axis 54. In addition thereto, the swivel arm 12 is rotatable about swivel axis 22, whereby the pivot arm 10 and the electronic display, together, are adjustably positionable about the swivel axis 22 independent of the adjustable positioning of the swivel arm 12. The pivot arm 10 also is pivotable about the pivot axis 46 and the pivot axis 48, whereby the pivot arm 10 and the electronic display 14, together, are adjustably positionable about the pivot axis 46 and pivot axis 48 independent of the adjustable positioning of the swivel arm 12.

Yet still, as shown in FIG. 1, the electronic display 14 is pivotable about the pivot axis 36, whereby the electronic display 14 is adjustably positionable about the pivot axis 36 independent of the adjustable positionings of the pivot arm 10. The electronic display further is pivotable about pivot axis 38, whereby the electronic display is further adjustably pivotable about the pivot axis 38 independent of the adjustable positioning of the pivot arm 10. The electronic display 14 also is rotatable about the swivel axis 30, whereby the electronic display 14 is adjustably positionable about the swivel axis 30 independent of the adjustable positionings of the pivot arm 10.

Notable characteristics of the illustrated embodiment in, for example, FIG. 2 include the fact that the swivel axes 54, 22, and 30 remain parallel to each other, and remain orthogonal to the translation axis 58, throughout all of the aforementioned adjustable positionings. Similarly, each of the pivot axes 46 and 48 and pivot axes 36 and 38 (FIG. 1) remain orthogonal to each of the swivel axes 54, 22, and 30 throughout all of the adjustable positionings. In addition thereto, it will further be noted that all of the pivot axes 46, 48, 36, and 38 remain non-orthogonal to the translation axis 58 through a range of adjustable positionings of the electronic display 14 and/or pivot arm 10. In a preferred method, the electronic display assembly is utilized to present audiovisual content to a person in a resting position. Accordingly, a preferred embodiment of an electronic display assembly is illustrated in FIG. 3 and includes the preferred embodiment of FIG. 1 combined with an apparatus 60 for receiving a person in a resting position. The apparatus broadly comprises, for example, a chair, recliner or bed and, in the field of providing a healthcare service, the apparatus preferably comprises a dental chair or operating table for supporting a patient receiving healthcare.

As will become apparent from review of FIG. 3, the electronic display 14 is suspended above, i.e., over, the apparatus 60 for convenient and unobstructed viewing by the person. Moreover, it thus will thus be appreciated that the electronic display 14 is coupled to a support such that the electronic display is adjustably positionable above the apparatus along each of three orthogonal axes, and such that the electronic display is adjustably positionable along each of these three axes independent of adjustable positioning of the electronic display along the other axes, thereby insuring a convenient and unobstructed view thereof by the person. Furthermore, in embodiments wherein the track is mounted to a wall or other support other than a ceiling, the electronic display 14 nevertheless preferably is still suspended above the apparatus 60 as shown in FIG. 3.

Aspects of the present invention include the presentation of audio and/or visual content to the person received in the apparatus 60. As used herein, such content is intended to be of broad meaning. Visual content may include graphical images of any level of detail. The graphical images can appear fixed in time on the display or can be moving or animated. The graphical images can be of live or recorded real, imaginary, or virtual world scenes such as that found in entertainment programs and informative news programs. The graphical images can include a view of a healthcare procedure in real time, can present expected results of a procedure, or can display or alternate between views before and after completion of a procedure or procedural step. Visual content also may include visual sensory stimulations as used in seeing ability tests, optometric evaluations, healthcare practices related to the eyes, psychological studies, or brain function mapping techniques. Visual content may also include navigable menus and folders such as implemented in conventional graphical user interfaces of computing systems. Internet browsing can be available with the use of the electronic display. Word processing, accounting software applications, and practice management proprietary or commercial software applications can be utilized by a patient or healthcare provider using the electronic display. The visual content may also represent the functionally operative portions of a touchscreen.

Accordingly, FIG. 3 further serves to illustrate a preferred embodiment for the wireless presentation of such content to the person while received in the apparatus 60. In particular, a send unit 62 is operative for wirelessly sending signals conveying content to be presented to the person received in the apparatus 60. The send unit may comprise, for example, a transmitter for broadcasting a wireless signal 64 to the receive unit. The transmitter can be any suitable transmitter such as a wireless router or RF transmitter, or an IR transmitter.

Figure 15:
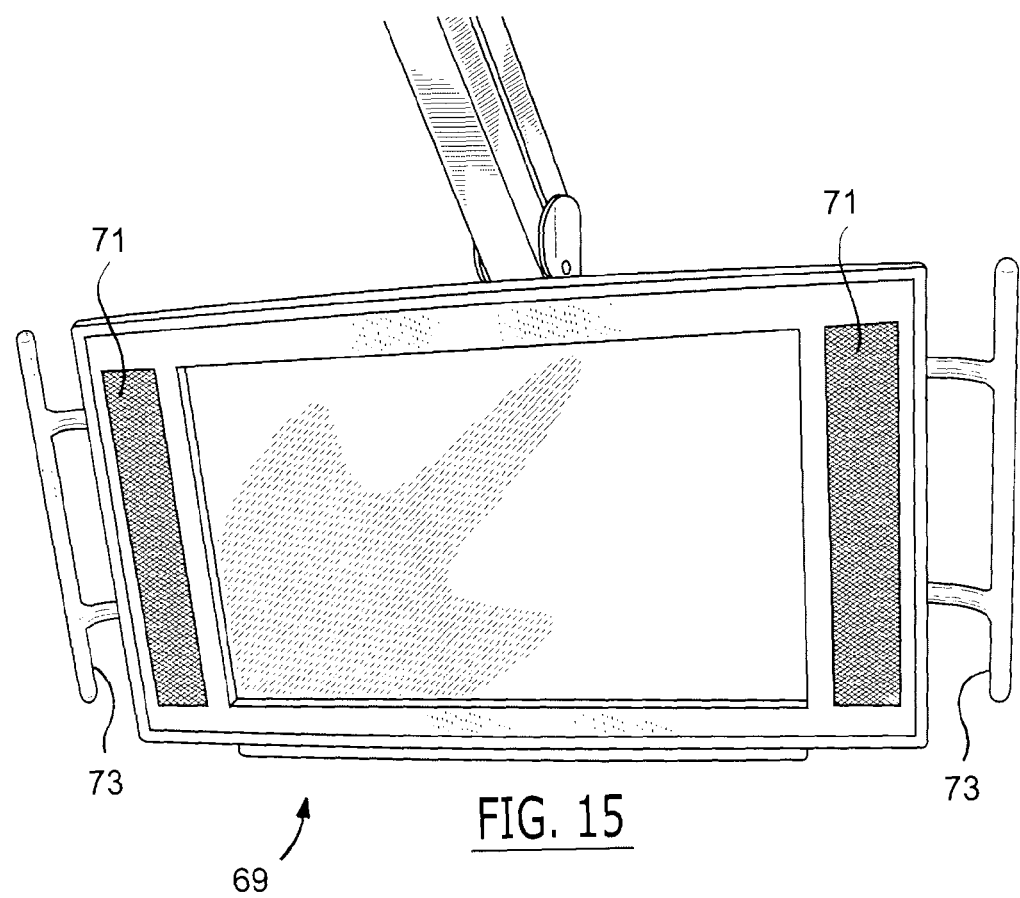
FIG. 15 is an elevational perspective view of another preferred embodiment of an electronic display incorporating a speaker component therein in accordance with one or more aspects of the present invention.

A receive unit comprising an antenna assembly 66 is disposed on the electronic display 14 and is operative to receive the signals for presenting of the visual content via the electronic display 14. A receive unit comprising wireless headphones 68 having antenna 70 also is worn by the person and is operative to receive the signals for presenting of the audio content via a speaker component of the headphones 68. The audio content presented by the headphones 68 may be independent of the visual content presented by the electronic display 14, or the audio content presented by the headphones 68 may accompany and be synchronized with the visual content presented by the electronic display 14, as desired. In variations of such embodiments, the electronic display 14 may include speakers and the antenna assembly 66 may receive signals for both audio content and visual content. In such variations, the electronic display 14 may include a speaker component for presenting the audio content to the person, or the electronic display 14 may include an output port such as a headphone jack for further communicating signals representing the audio content. In other variations, a speaker component may be embedded in the headrest 72 of the apparatus 60 for presenting of the audio content. A preferred embodiment of an electronic display 69 incorporating a speaker component comprising speakers 71 therein is illustrated in FIG. 15. Moreover, this preferred embodiment further includes handles 73 disposed on opposite sides of the electronic display 69 in order to facilitate the adjustable positioning by the viewer.

The send unit 62 is shown in FIG. 3 as being attached to a wall; however, the send unit 62 may be disposed anywhere so long as the receive units 66,68 are within its transmission range. Alternative locations include being secured to the support to which the track 50 is mounted.

Figure 4:
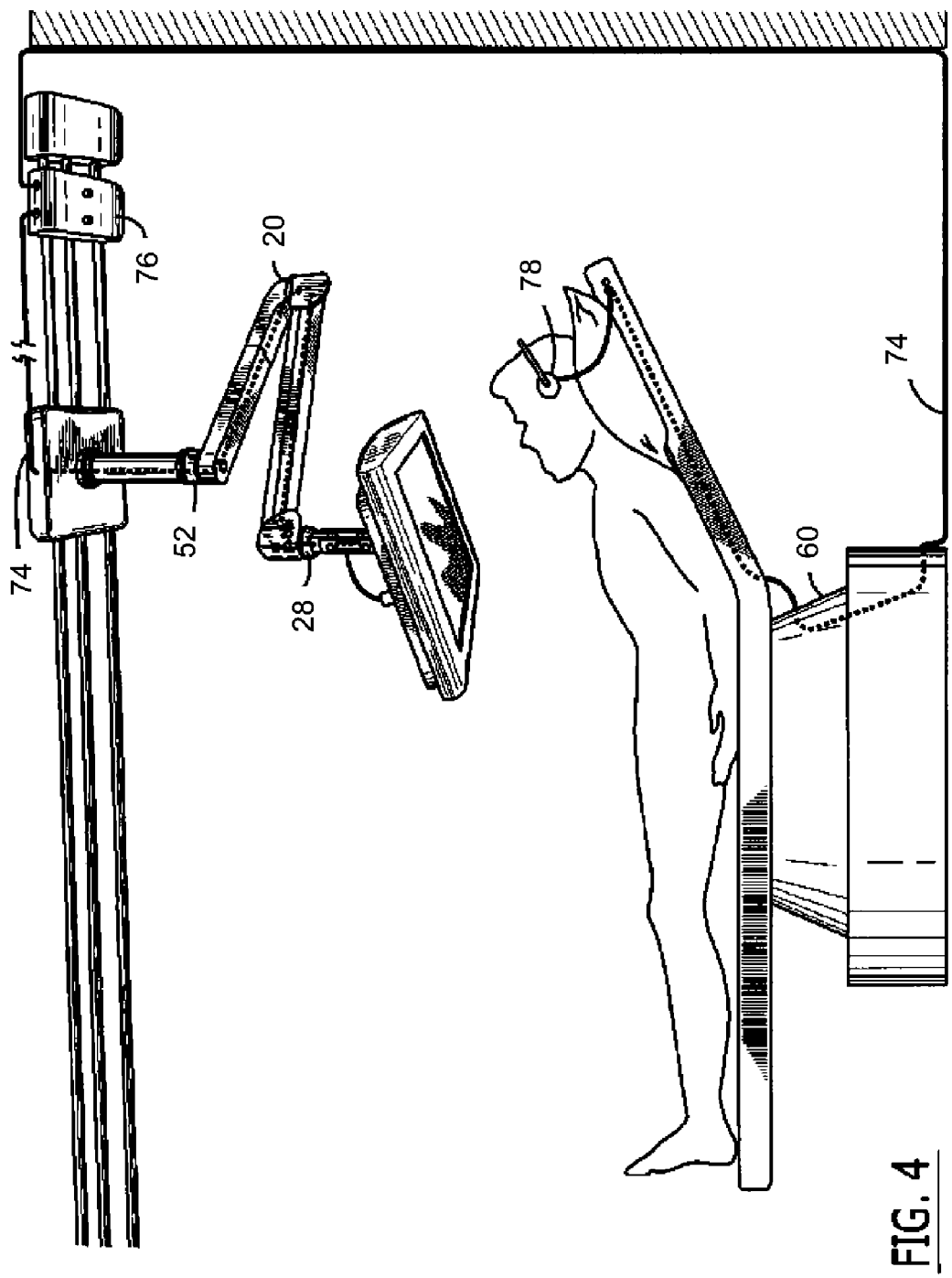
FIG. 4 is another perspective elevational view of a preferred embodiment of an electronic display assembly in accordance with one or more aspects of the present invention.

The send unit further may be disposed in electronic communication with said receive unit by a cable or wire connection of any suitable type for carrying signals from the send unit to the receive unit. In embodiments of the system that include such a connection, the connection is preferably constructed, arranged, and routed to connect the send and receive units through a pathway internal to the overhead structure that supports the receive unit. Such an arrangement and routing provides for aesthetic elegance in the environment of the system and, particularly in a healthcare environment, avoids cluttering of a patient care area. This well complements a variable support assembly by allowing freedom of movement of a display without dangling wires congesting the immediate area of a healthcare provider and patient. This variation is illustrated in FIG. 4, where cable 74 is shown extending between, and connecting in electronic communication, both the send unit 76 with a receive unit in the form of an input jack (not shown) of the electronic display 14, and the send unit 76 with a receive unit in the form of an amplifier embedded in the apparatus 60 and having input and output jacks 78. With additional regard to this variation, the cable leading to the electronic display 14 preferably is disposed internal to at least the swivels 52, 20, and 28, whereby the cable does not inhibit the range of motion that the electronic display 14 otherwise enjoys.

With regard to another variation of the invention, the range of rotation of each swivel is limited, for example limited to less than full rotation, in order to avoid twisting of a cable internal thereto. Such a variation comprises a bearing projecting from a detent under the force of a spring to lock and arrest rotation at an extreme of an allowed range.

Figure 5:
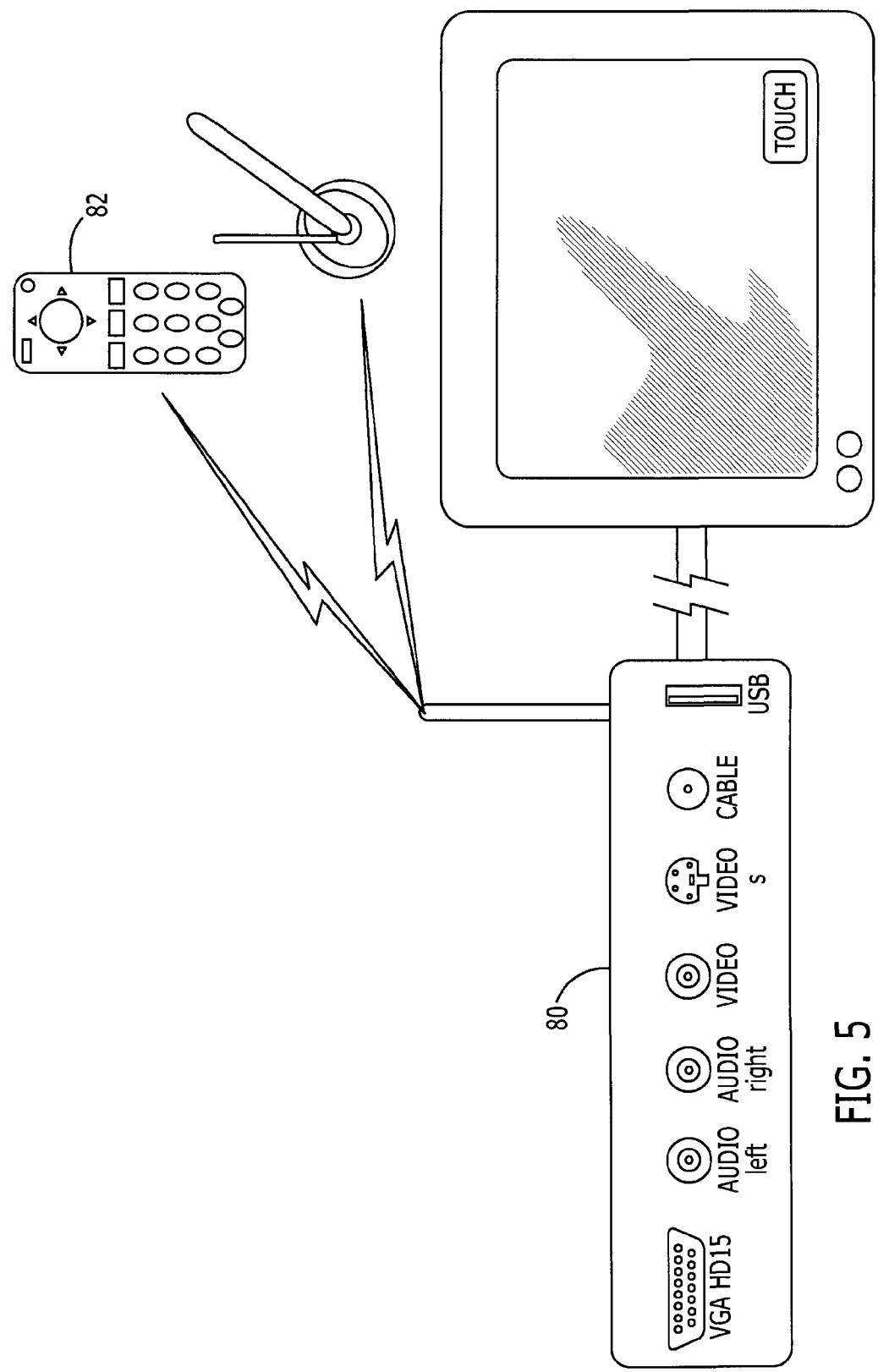
FIG. 5 is an illustration of components of preferred embodiments of an electronic display assembly in accordance with one or more aspects of the present invention.

The send unit 76 includes multiple inputs and is capable of receiving content from a range of disparate or related sources and sending signals for the various content to the receive unit in a unitary fashion. The range of sources, within the scope of the invention here described, includes without limitation, any electronic accessory or interface that produces or relays signals that convey visual and/or audio content, including, but is not limited to: a video cassette recorder (VCR) or player; a digital video disk (DVD) recorder or player; a computer; a computerized network, router, or interface; a television signal receiver or tuner; a cable signal receiver or tuner; a satellite signal receiver or tuner; a video camera; and digital X ray equipment. Thus, some multiple inputs of the send unit 76 may include, for example, an S-video input, a cable input, a USB input, and an RCA input. The exemplary embodiment 80 of the send unit illustrated in FIG. 5 includes a patch panel with ports for VGA fifteen-pin, RCA (left audio, right audio, and video), S-video, USB, and commercial cable inputs. These are exemplary, and other types of input ports are within the scope of the invention.

Figure 13:
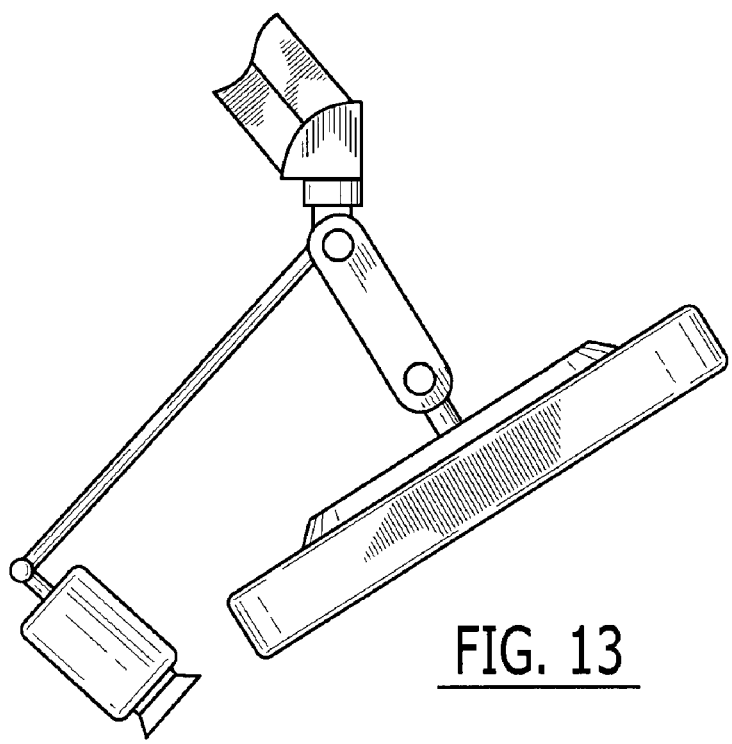
FIG. 13 is an elevational side view of a preferred embodiment of an electronic display having an electronic input member mounted thereon in accordance with one or more aspects of the present invention.
Figure 14:
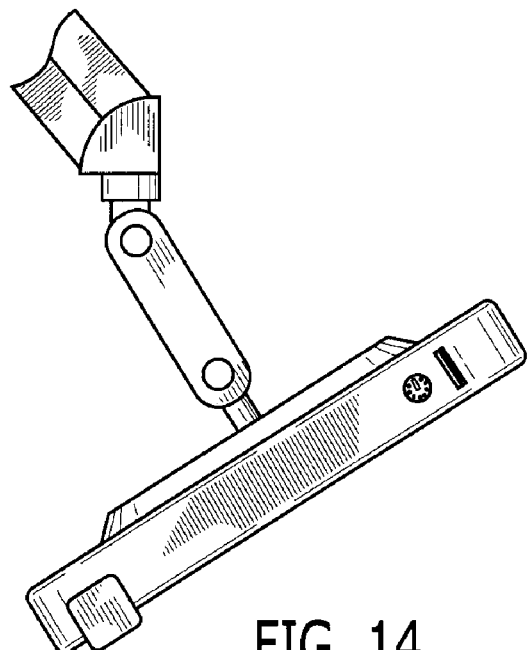
FIG. 14 is an elevational side view of another preferred embodiment of an electronic display incorporating an electronic input member therein in accordance with one or more aspects of the present invention.

In accordance with aspects of the present invention, either the electronic display 14 or the subassembly 26 connecting the electronic display 14 to the pivot arm 10 includes an electronic input member for acquiring or receiving data. In this respect, the electronic input member may include in preferred embodiments of the present invention, for example: a touchscreen of the electronic display for receiving electronic input by a person's touch; an antenna disposed on the electronic display for receiving wireless data transmissions; an electronic communications port included in the electronic display for receiving data such as, for example, a USB port, a firewire port, a serial port, a parallel port, or a PS/2 port; and a data acquisition device mounted to the electronic display or subassembly, the data acquisition device including, for example, a sensor, a camera, or a microphone. Exemplary embodiments of electronic displays including electronic input members are illustrated in FIGS. 13-14.

In accordance with aspects of the present invention, an electronic input member also may be included that is physically independent from the electronic display and subassembly. In this respect, the electronic input member may be detachably mounted to a support accessible to the person viewing the electronic display. The electronic input member may include in preferred embodiments of the present invention, for example: a conducting contact; an electromechanical switch; a mouse; a handheld device; a joystick; a keyboard; a keypad; and a wireless device such as a remote control.

In certain preferred embodiments that include an electronic input member for receiving or acquiring data, a computer or other electronic circuitry preferably is provided in electronic communication with the electronic input member for processing data received or acquired from the electronic input member. In such embodiments, the computer may store and analyze the data from the electronic input member. Results of the analysis then may be presented via the electronic display. If the electronic input member is a camera, video acquired by the camera may be captured and then displayed on the electronic display. In other such embodiments, the computer may simply manage presentation of video on the electronic display, and the data from the electronic input member may represents instructions for managing the presentation of the video on the electronic display. The computer further may be coupled to the carriage for movement therewith, and may even be disposed within a housing of the electronic display. Alternatively, the computer may be remotely located to the electronic display and, thus, stationary with respect to movement of the carriage.

With reference again to FIG. 5, an electronic input member comprising a wireless remote control 82 is shown. The remote control 82 preferably communicates wirelessly with the send unit 80 (i.e., the computer or other electronic circuitry in this illustration), for controlling the presentation of the audio and/or video content. Control of the content may include, for example, selecting for presentation a movie, a television station a cable station, a music video, an educational video, a cartoon. Such control may further include, for example, navigating the Internet, including reading email and composing email, especially where the electronic input member includes an arrangement of alphanumeric keys. In this case, a keyed input device may be provided. In any event, the person viewing the electronic display (and/or a healthcare provider in the context of providing healthcare to a patient viewing the electronic display) preferably has some control over the content presented by the electronic display.

In a particular preferred embodiment, the electronic input member for receiving input regarding controlling presentation of the content presented by the electronic display communicates directly with a receive unit which, in turn, is operative, in response to the input received by the electronic input member, to send signals to the send unit for controlling presentation of visual content by the electronic display. In this regard, the send unit then is operative for receiving the signals for controlling presentation of visual content from the receive unit and responding accordingly. This reverse communications system is useful when the send unit is disposed remote from, and possibly out of range to, the electronic input member.

In accordance with aspects of the present invention, particular content to be presented by the electronic display is actually selected by use of an electronic input member and then delivered to the electronic display in response to such selection. Furthermore, the content preferably is selected by each patient from a plurality of available selections and delivered on demand at the time of the selection. This is particularly useful in a healthcare environment, wherein a plurality of patients may be provided from a central distribution source with particular content upon demand.

Figure 6:
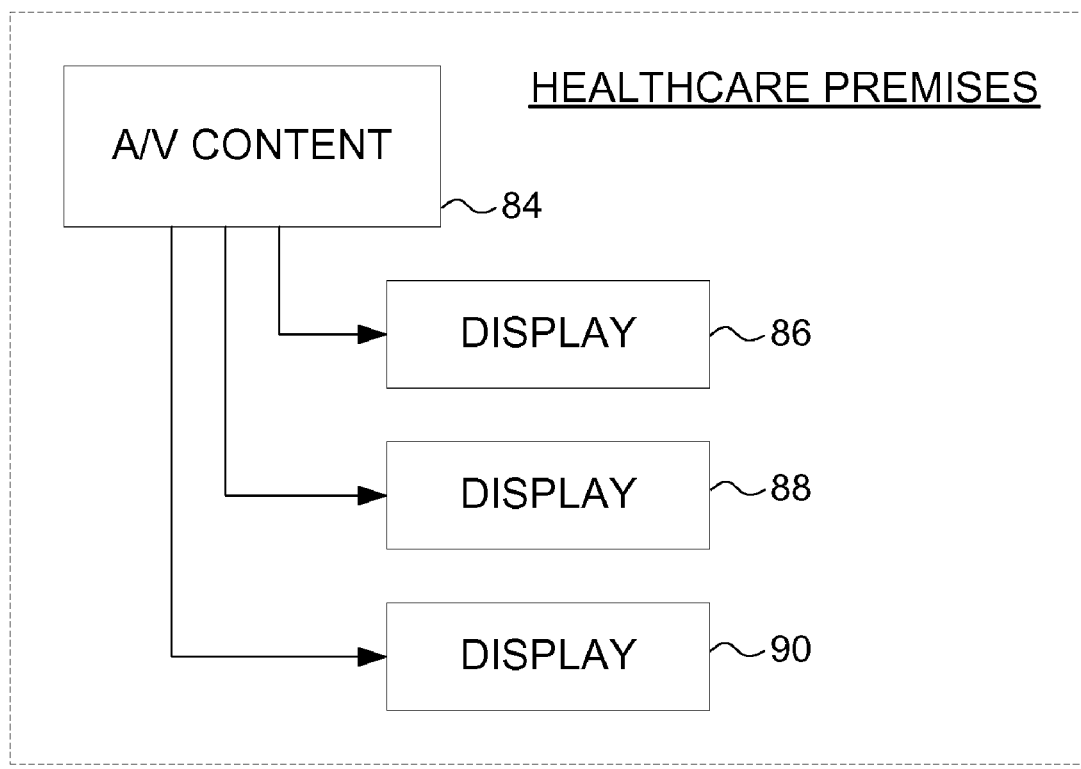
FIG. 6 is an illustration of a preferred embodiment of delivering video to electronic displays in accordance with one or more aspects of the present invention.

The contemporaneous delivery of content is schematically illustrated in FIG. 6, wherein the audio and/or video content is centrally stored at 84 and then delivered to each of displays 86,88,90. The central distribution system preferably includes at least one data storage device for digitally storing the available content selections. The data storage device may include, for example, a computer readable medium, computer memory, or one or more optical discs. Each of the displays represents an electronic display assembly in accordance with the present invention.

Figure 7:
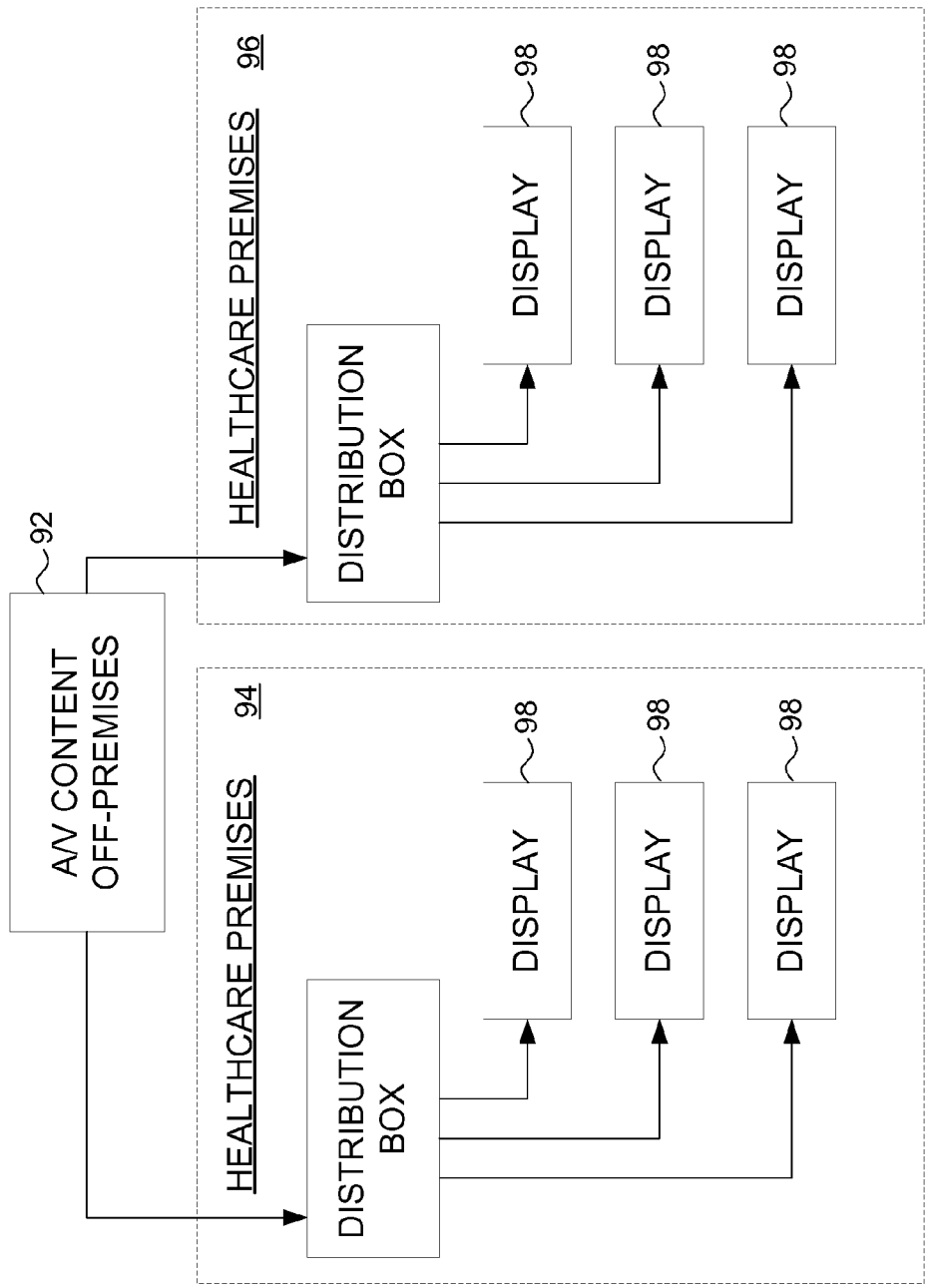
FIG. 7 is an illustration of another preferred embodiment of delivering video to electronic displays in accordance with one or more aspects of the present invention.

As shown in FIG. 6, the content is centrally stored on premises of the healthcare facility having the multiple electronic displays 86,88,90. Alternatively, as shown in FIG. 7, the content is centrally stored at a central distribution system 92 located off premises with respect to the multiple healthcare facilities 94,96, each of which utilizes the electronic display assemblies 98 of the present invention in providing healthcare service. Communications of content from the central distribution system to each healthcare facility may occur via the Internet. Moreover, the content may be communicated in a digital format as a real time signal or data flow, or as a video file or a video file portion such as, for example, a program clock reference (PCR) stamped moving picture experts group (MPEG) file.

In accordance with a particular aspect of the present invention relating to the central distribution system, a third-party party preferably is responsible for providing content to each of the healthcare facilities for presentation on the electronic display assemblies of the present invention. Moreover, this third-party preferably is not in the business of providing healthcare services but, instead, is a service provider to the healthcare facilities. As such, the content preferably is provided by the third-party under a subscription contract or on a pay-per-view basis.

In accordance with other aspects of the present invention, and again with particular reference to the provision of healthcare service, an audio or audiovisual communications system preferably is provided for use between a patient receiving a healthcare service and a healthcare provider. The audio communications system includes a speaker component for providing auditory content to the patient while receiving the healthcare service, an audio component in communication with the speaker component for providing the auditory content to the speaker component, and an input controller accessible to the healthcare provider for controlling the provision of the auditory content to the patient.

The speaker component may comprises, for example, headphones or earphones for wearing by the patient. The speaker component alternatively may comprise, for example, a speaker coupled to, or embedded in, the apparatus. If embedded in the apparatus, the speaker preferably is embedded in a headrest of the apparatus in order to be in close proximity to a patient's head. The audio component preferably communicates wirelessly with the speaker component, in which case the speaker component preferably includes a wireless signal receiver for receiving signals conveying the auditory content. In this regard, the wireless signal receiver may include a radio-frequency (RF) or infrared (IR) signal receiver.

Conveniently, the input controller comprises a foot actuated switch or pedal, whereby the healthcare provider may varying the volume of, or altogether mute, the auditory content provided to the patient while receiving the healthcare service in order that the patient will hear the healthcare provider speaking. In this respect, the input controller essentially comprises a volume control device. Alternatively, a microphone component may be provided by which the healthcare provider speaks to the patient through the speaker component. In doing so, the microphone component preferably communicates directly with the audio component for conveying the voice of the healthcare provider to the patient, or the microphone component communicates directly with the speaker component for conveying the voice of the healthcare provider to the patient. Furthermore, the auditory content otherwise being provided to the patient preferably is lowered, or altogether muted, when the microphone is activated for recording the voice of the healthcare provider. In this context, the microphone preferably is activated using an input controller of the healthcare provider which, again, preferably comprises a foot actuated switch or pedal. Furthermore in this context, the input controller is seen as being, again, a volume control device.

The input controller of the healthcare provider may include the ability to select and manage the content provided to the patient. Alternatively, or in addition thereto, the patient preferably is provided an input controller for controlling, by the patient, the provision of the auditory content. This may further include the ability to select the audio or audiovisual content to be presented on the electronic display, in which case the input controller also comprises an aforementioned electronic input member.

Similar to the aforementioned central distribution system of FIGS. 6 and 7, in preferred embodiments the audio communications system includes a storage component wherein a plurality of auditory content selections are stored. Furthermore, the storage component is disposed in electronic communication with the audio component for providing, by the audio component, any one of the auditory content selections to the speaker component. The storage component may include, for example, a digital jukebox and/or a DVD jukebox. The storage component also may be a computer readable medium, in which case the audio component preferably comprises a computer. Moreover, the storage component may be stored on premises or off premises, either by the healthcare facility entity or a third-party, similar to the aforementioned video delivery system discussed above in connection with FIG. 6-7. In any event, in such preferred arrangements, the patient using the input controller may (1) conveniently select that auditory content desired while receiving healthcare, and (2) conveniently adjust the volume of the auditory content provided.

Figure 8:
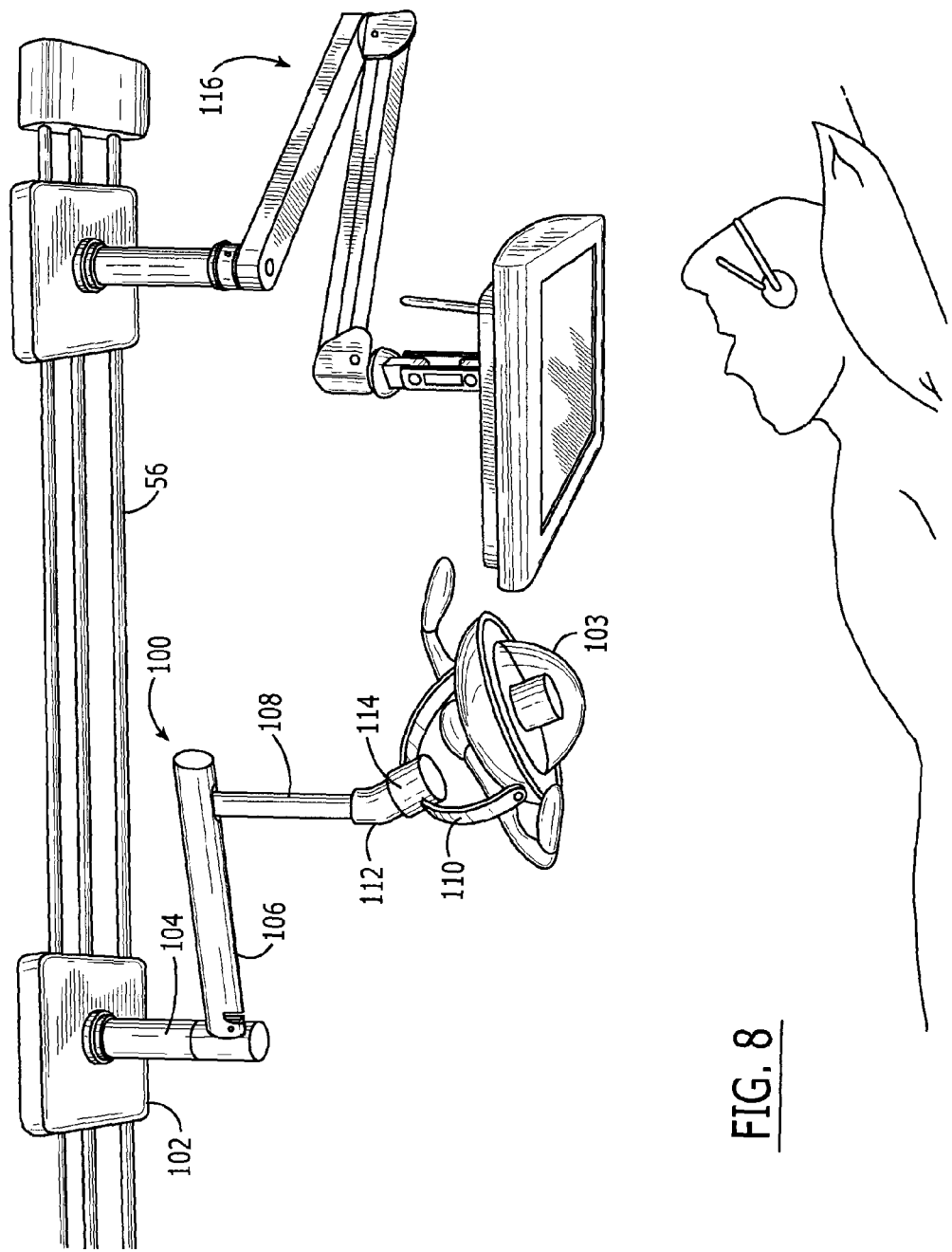
FIG. 8 is a perspective elevational view of a preferred embodiment of an electronic display and lighting arrangement in accordance with one or more aspects of the present invention.

Use of the electronic display assembly of FIGS. 1-4 in a healthcare environment is illustrated in FIG. 8. In this regard, the healthcare being provided to the patient comprises dental healthcare. To aid the healthcare provider in the dental healthcare service, a lighting assembly 100 is provided for illumination of the patient. In particular, as seen in FIG. 8, an electronic display and lighting arrangement includes the electronic display assembly of FIGS. 1-4 as well as another carriage 102 coupled to the track having a light 103 coupled to the second carriage 102. This second carriage can be variably positioned along the track separately from the first carriage of the electronic display assembly. A support assembly couples the light to the second carriage and travels with the second carriage along the track. This support assemble includes three support arms. A first support arm 104 is attached to and extends vertically downward from the second carriage. A second support arm 106 is pivotably connected to the first support arm and extends generally horizontally therefrom. A third support arm 108 is pivotably connected to and extends generally vertically downward from the second support arm 106. A support bracket 110 is connected to the end of the third support arm at a bend 112 therein by a swivel 114, and the light is pivotably connected between and to opposed ends of the bracket. As a result of the support assembly, the light enjoys: vertical positioning based on the pivotable connection of the first support arm 104 to the second support arm 106, and the pivotable connection of the second support arm 106 to the third support arm 108; and rotation and pivoting on the end of the third support arm 108 for directional placement of a beam of light. The light also enjoys translational movement along the track independent of the positioning of the electronic display assembly 116.

Figure 9:
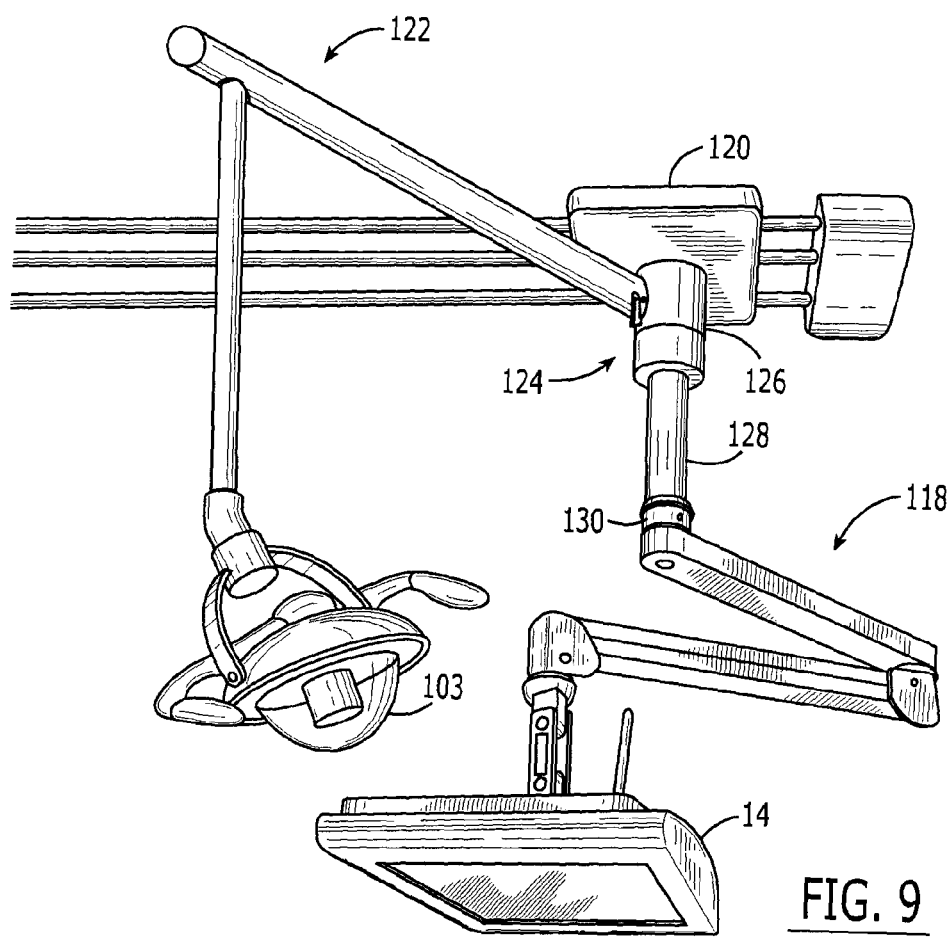
FIG. 9 is another perspective elevational view of a preferred embodiment of an electronic display and lighting arrangement in accordance with one or more aspects of the present invention.

A similar electronic display and lighting arrangement is illustrated in FIG. 9. This arrangement generally includes the combination of an electronic display assembly 118 of the present invention and a lighting assembly 122 supported by a single carriage 120. In this regard, the electronic display and light share a common two-stage vertical support member 124 that extends downwardly from the carriage. The lighting assembly 122 is coupled to the upper stage of the common vertical support member 124 by a swivel 126, and the electronic display 118 is coupled to the lower stage 128 of the common vertical support member 124 by another swivel 130. Independence of these couplings permits the light to be rotated about the common vertical support member independent of rotation of the electronic display about the common vertical support member.

Figure 10:
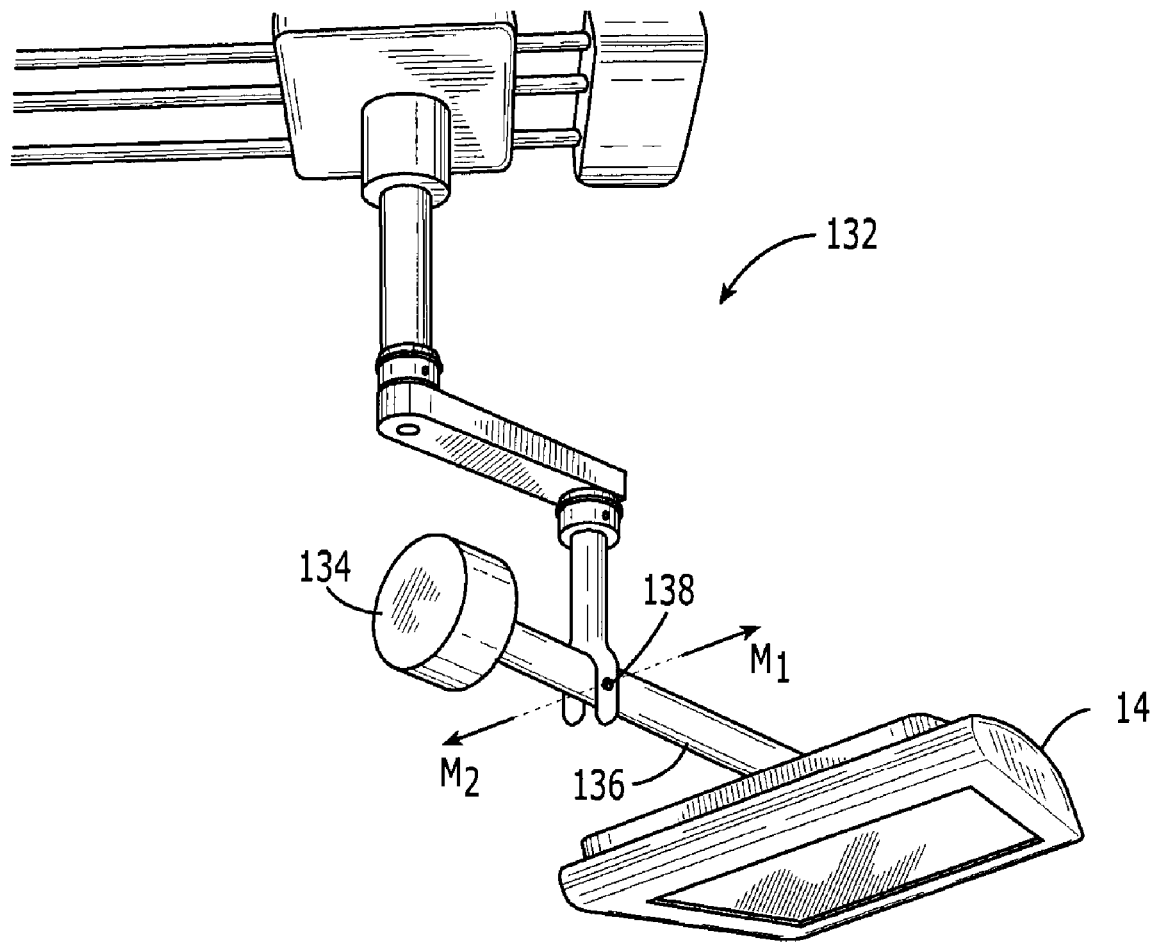
FIG. 10 is yet another perspective side view of another preferred embodiment of an electronic display and lighting arrangement in accordance with one or more aspects of the present invention.

FIG. 10 illustrates another preferred embodiment in accordance with an aspect of the present invention. In this regard, an electronic display assembly 132 includes a counterweight 134 coupled to a pivot arm 136 such that the counterweight 134 opposes the electronic display about the pivot point 138. Preferably, the counterweight 134 has a mass greater than that of the electronic display and is located closer to the pivot point 138 than the electronic display, whereby the counterweight has a moment M1 about the pivot point that is within at least an order of magnitude of a moment M2 of the electronic display about the pivot point. As will be apparent to those having ordinary skill in the art, the counterweight 134 reduces the effort required for adjustably positioning the electronic display. The counterbalance features may be utilized with any electronic display irrespective of the field of use of the electronic display. Accordingly, an electronic display assembly including the counterbalance feature may be utilized, for example, in home entertainment or healthcare services.

When an electronic display assembly is utilized in conjunction with providing healthcare service, a computer system preferably is provided that includes healthcare software having data pertaining to the healthcare service received by a patient. Furthermore, the computer system preferably is disposed in electronic communication with the electronic display for presenting, by the electronic display, in accordance with the healthcare software, video output from the computer system. The video presented by the electronic display as output by the computer preferably includes information regarding the healthcare being provided, a healthcare record of the patient, and/or information regarding a healthcare service received by the patient. Additionally provided is an electronic input member for use by the healthcare service provider for interfacing with the healthcare software of the computer system. The electronic input member may communicate with said computer system through the electronic display suspended of the present invention. In this context, the electronic input member preferably comprises a touchscreen of the electronic display. Alternatively, the electronic input member comprises a keypad, a keyboard, a mouse, or an electromechanical switch.

Moreover, when an electronic display assembly is utilized in conjunction with providing healthcare service, then, in accordance with an aspect of the present invention, the electronic display preferably includes a display screen and a protective shield that covers and protects the display screen. The display screen preferably comprises a touchscreen, and the touchscreen may be an infrared touchscreen or a touchscreen that utilizes projected capacitive technology. The protective shield preferably is transparent and is removably attached to the electronic display, whereby the protective shield may be removed and replaced from time-to-time.

Figure 11A:
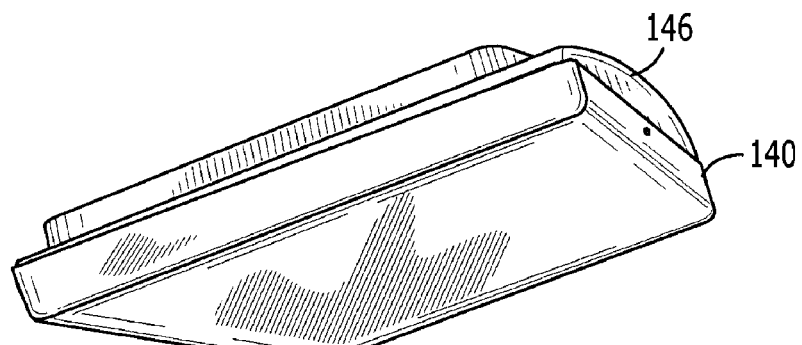
FIG. 11A is a perspective elevational view of a preferred embodiment of an electronic display in accordance with one or more aspects of the present invention.
Figure 11B:
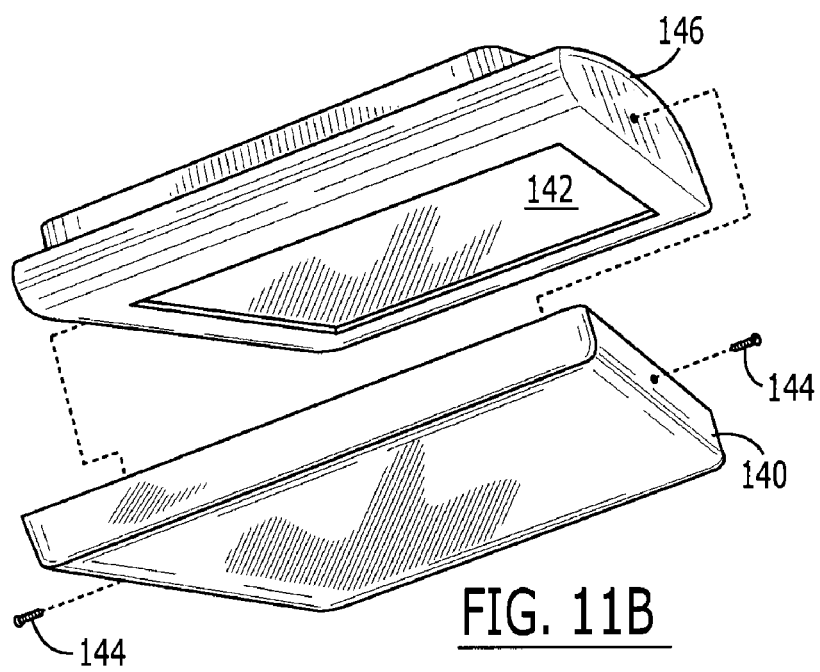
FIG. 11B is an exploded view of the electronic display of FIG. 11A.

An illustration of the protective shield 140 covering the display screen 142 is shown in FIG. 11A. An exploded view thereof is shown in FIG. 11B. As shown, screws 144 removably secure the protective shield 140 to a housing 146 of the electronic display in covering relation to the display screen 142. The protective shied preferably is formed from a polycarbonate material sold by General Electric Corporation under the mark LEXAN; however, the protective shield may also be formed from a plastic or thermoplastic material. In any event, the material forming the protective shield preferably is a chemical-resistant material that includes scratch resistant, antistatic, and antiglare characteristics. The protective shield also preferably is impact resistant and waterproof. The protective shield further preferably is impenetrable to pathogens and capable of being sterilized with a disinfectant for use in the healthcare environment.

For aesthetic purposes, the protective shield preferably is screen printed on an inside surface thereof, whereby a solid black appearance is presented to a viewer when the underlying display screen is not illuminated. A polarizing filter and/or a Bernoulli lens also preferably is disposed between the display screen and the protective shield for enhancing the image of the display.

Figure 12:
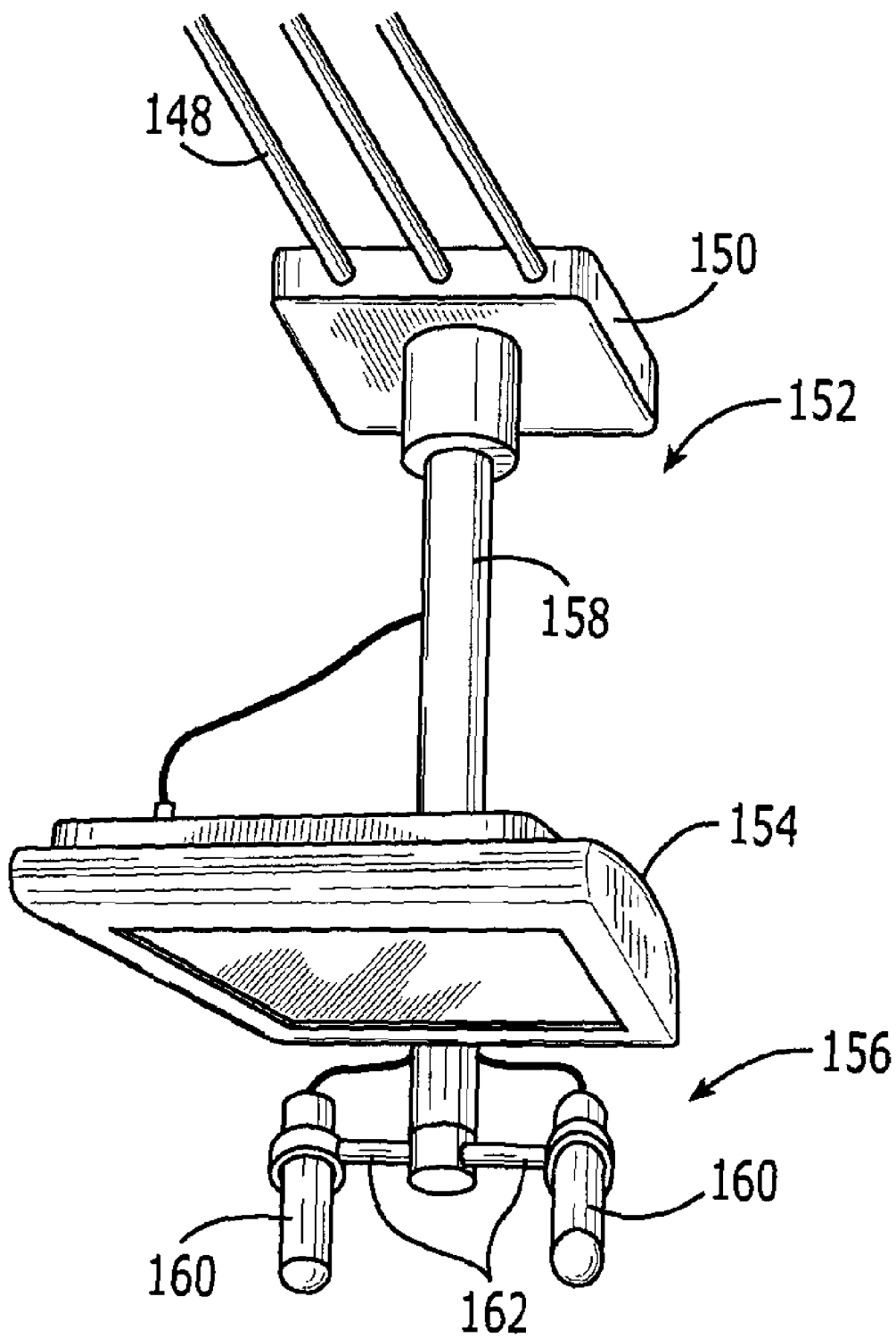
FIG. 12 is a perspective elevational view of a current commercial product utilized in a method and system embodying one or more aspects of the present invention.

A basic commercial product in the healthcare market utilized in a system that embodies at least one aspect of the present invention is illustrated in FIG. 12. This product comprises an overhead track 148, a carriage 150 coupled to the track 148, and a support assembly 152 to which is coupled a display 154 and a light assembly 156. The carriage 150 is variably positionable along the track 148, and the product includes a generally vertical elongate member 158 connected to and extending below the carriage 150. The display 154 is coupled to the elongate member 158 for pivoting movement about a horizontal axis for selective orientation of the display 154. The light is coupled to a lower end of the elongate member 158 and comprises an opposing pair of light units 160. Each light unit 160 is connected to a respective extension 162 depending from the elongate member 158, and each light unit 160 can be variably orientated for direction of its light beam. In similar manner to the electronic display and lighting arrangement of FIG. 9, the carriage 150 in operation carries the display 154 and the light units 160 along the track 148 for variable positioning to allow selective placement of the display 154 and the light units 160 above a patient.

The present invention has been described in relation to particular embodiments which are intended in all respects to be illustrative rather than restrictive. Alternative embodiments will become apparent to those skilled in the art to which the present invention pertains without departing from its spirit and scope. Furthermore, any sequence(s) and/or temporal order of steps of various processes described and claimed herein are those considered to be the best mode contemplated for carrying out the present invention. Thus, it should be understood that, although steps of various processes may be shown and described as being in a preferred sequence or temporal order, the steps of any such processes are not limited to being carried out in any particular sequence or order, absent a specific indication of such to achieve a particular intended result. Indeed, the steps in such processes generally may be carried out in various different sequences and orders while still falling within the scope of the present invention. Accordingly, the scope of the present invention is defined by the appended claims rather than the foregoing description.

What is claimed is:

1. An electronic display and lighting arrangement for viewing by, and illumination for, a dental patient received in a resting position in a dental chair, comprising,
   (a) an electronic display assembly comprising,
      (i) a first carriage coupled to an overhead track and movable along a translation axis,
      (ii) a first pivot arm coupled to said first carriage such that said first pivot arm is variably positionable in different inclinations to a horizontal plane, and
      (iii) an electronic display including a display screen, said electronic display being coupled to said first pivot arm and adjustably positionable both,
         (A) with said first carriage, along said translation axis, by movement of said first carriage, and
         (B) with said first pivot arm, relative to said horizontal plane, by movement of said first pivot arm,
      (iv) wherein said electronic display is coupled to said first pivot arm such that said display screen may be disposed in a horizontal orientation,
   (b) a lighting assembly comprising,
      (i) a second carriage movable in a direction parallel to said translation axis, and
      (ii) a light coupled to said second carriage and adjustably positionable in said direction by movement of said second carriage, and
   (c) a dental chair for receiving a dental patient in a resting position, said dental chair including a headrest for receiving a head of the dental patient,
   (d) wherein,
      (i) illumination by said light is provided for the dental patient in the resting position received in said dental chair, and
      (ii) said electronic display is adjustably suspendable vertically above said headrest of said dental chair, with said display screen disposed in a horizontal orientation, for viewing by the dental patient received in said dental chair, without said light obstructing viewing of said electronic display by the dental patient.

2. The arrangement of claim 1, wherein said second carriage is coupled to said overhead track.

3. The arrangement of claim 2, wherein said overhead track is mounted to a ceiling.

4. The arrangement of claim 1, wherein said first carriage and said second carriage are movable in the direction parallel to said translation axis independent of one another.

5. The arrangement of claim 1, wherein said lighting assembly further includes a second pivot arm extending between and coupled to said second carriage and said light, said second pivot arm pivotable about a second pivot axis, said light being adjustably movable about said second pivot axis by movement of said second pivot arm about said second pivot axis.

6. The arrangement of claim 1, wherein the coupling of said first pivot arm to said first carriage includes a first swivel member such that said first pivot arm is configured to be variably swiveled about a first swivel axis of said first swivel member relative to said first carriage.

7. The arrangement of claim 6, wherein the coupling of said electronic display to said first pivot arm includes a second swivel member such that said electronic display is configured to be variably swiveled about a second swivel axis of said second swivel member relative to said first pivot arm.

8. An electronic display and lighting arrangement for viewing by, and illumination for, a dental patient received in a resting position in a dental chair, comprising,
   (a) an electronic display assembly comprising,
      (i) a first carriage coupled to an overhead track and movable along a translation axis,
      (ii) a first pivot arm coupled to said first carriage such that said first pivot arm is variably positionable in different inclinations to a horizontal plane, and
      (iii) an electronic display including a display screen, said electronic display being coupled to said first pivot arm and adjustably positionable both,
         (A) with said first carriage, along said translation axis, by movement of said first carriage, and
         (B) with said first pivot arm, relative to said horizontal plane, by movement of said first pivot arm, (iv) wherein said electronic display is coupled to said first pivot arm such that said display screen may be disposed in a horizontal orientation,
(b) a lighting assembly comprising,
  (i) a second carriage movable in a direction parallel to said translation axis, and
  (ii) a light coupled to said second carriage and adjustably positionable in said direction by movement of said second carriage, and
(c) a dental chair for receiving a dental patient in a resting position, said dental chair including a headrest for receiving a head of the dental patient,
(d) wherein,
  (i) illumination by said light is provided for the dental patient in the resting position received in said dental chair, and
  (ii) said electronic display is adjustably suspended vertically directly above said headrest of said dental chair, with said display screen disposed in an orientation facing said headrest, for viewing by the dental patient received in said dental chair, without said light obstructing viewing of said electronic display by the dental patient.

9. The arrangement of claim 8, wherein said second carriage is coupled to said overhead track.

10. The arrangement of claim 9, wherein said overhead track is mounted to a ceiling.

11. The arrangement of claim 8, wherein said first carriage and said second carriage are movable in the direction parallel to said translation axis independent of one another.

12. The arrangement of claim 8, wherein said lighting assembly further includes a second pivot arm extending between and coupled to said second carriage and said light, said second pivot arm pivotable about a second pivot axis, said light being adjustably movable about said second pivot axis by movement of said second pivot arm about said second pivot axis.

13. The arrangement of claim 8, wherein the coupling of said first pivot arm to said first carriage includes a first swivel member such that said first pivot arm is configured to be variably swiveled about a first swivel axis of said first swivel member relative to said first carriage.

14. The arrangement of claim 13, wherein the coupling of said electronic display to said first pivot arm includes a second swivel member such that said electronic display is configured to be variably swiveled about a second swivel axis of said second swivel member relative to said first pivot arm.

* * * * *

UNITED STATES PATENT AND TRADEMARK OFFICE
CERTIFICATE OF CORRECTION

| | | |
|---|---|---|
| PATENT NO. | : 7,828,252 B2 | Page 1 of 1 |
| APPLICATION NO. | : 11/275886 | |
| DATED | : November 9, 2010 | |
| INVENTOR(S) | : Shannon G. Parsons | |

It is certified that error appears in the above-identified patent and that said Letters Patent is hereby corrected as shown below:

Column 23, line 17, change the word --suspended-- to --suspendable-- so that line 17 reads as follows:
"(ii) said electronic display is adjustably suspendable ver-"

Signed and Sealed this
First Day of March, 2011

David J. Kappos
*Director of the United States Patent and Trademark Office*